United States Patent
Bechard et al.

(10) Patent No.: US 11,351,118 B2
(45) Date of Patent: Jun. 7, 2022

(54) METHODS FOR AMELIORATING INFUSION REACTIONS

(71) Applicant: ARBUTUS BIOPHARMA CORPORATION, Burnaby (CA)

(72) Inventors: Jeffrey P. Bechard, Surrey (CA); Wayne J. Wallis, Seattle, WA (US)

(73) Assignee: ARBUTUS BIOPHARMA CORPORATION, Burnaby (CA)

( * ) Notice: Subject to any disclaimer, the term of this patent is extended or adjusted under 35 U.S.C. 154(b) by 0 days.

(21) Appl. No.: 16/470,490

(22) PCT Filed: Dec. 20, 2017

(86) PCT No.: PCT/US2017/067664
§ 371 (c)(1),
(2) Date: Oct. 31, 2019

(87) PCT Pub. No.: WO2018/119115
PCT Pub. Date: Jun. 28, 2018

(65) Prior Publication Data
US 2019/0328664 A1   Oct. 31, 2019

Related U.S. Application Data

(60) Provisional application No. 62/437,537, filed on Dec. 21, 2016.

(51) Int. Cl.
| | | |
|---|---|---|
| *A61K 9/127* | (2006.01) | |
| *A61P 29/00* | (2006.01) | |
| *A61K 9/00* | (2006.01) | |
| *A61K 31/192* | (2006.01) | |
| *A61K 47/10* | (2017.01) | |
| *A61K 47/24* | (2006.01) | |
| *C12N 15/11* | (2006.01) | |
| *A61K 45/06* | (2006.01) | |

(52) U.S. Cl.
CPC ............ *A61K 9/127* (2013.01); *A61K 9/0019* (2013.01); *A61K 31/192* (2013.01); *A61K 47/10* (2013.01); *A61K 47/24* (2013.01); *A61P 29/00* (2018.01); *C12N 15/111* (2013.01); *A61K 45/06* (2013.01)

(58) Field of Classification Search
CPC .... A61K 9/127; A61K 9/0019; A61K 31/192; A61K 47/10; A61K 47/24; A61K 45/06; A61P 29/00; C12N 15/111; C12N 2310/14; C12N 2320/31; C12N 2320/53
See application file for complete search history.

(56) References Cited

U.S. PATENT DOCUMENTS

| | | | |
|---|---|---|---|
| 2002/0136759 A1* | 9/2002 | Szebeni | A61K 38/42 424/450 |
| 2005/0136759 A1* | 6/2005 | Shannon | D21H 17/59 442/59 |
| 2005/0143336 A1* | 6/2005 | Ramesh | A61K 31/525 514/44 A |
| 2005/0276785 A1 | 12/2005 | Groetzbach et al. | |
| 2007/0054873 A1 | 3/2007 | Maclachlan et al. | |
| 2007/0134339 A1 | 6/2007 | Jenkins et al. | |
| 2010/0055169 A1* | 3/2010 | Dande | C07C 219/06 514/1.1 |
| 2010/0286222 A1 | 11/2010 | Hammock et al. | |
| 2016/0095830 A1 | 4/2016 | Pavliv et al. | |
| 2016/0122759 A1 | 5/2016 | Kasperkovitz et al. | |

FOREIGN PATENT DOCUMENTS

| | | |
|---|---|---|
| WO | 2011034798 A1 | 3/2011 |
| WO | 2016054421 A1 | 4/2016 |

OTHER PUBLICATIONS

Moghami et al. (Drug discovery today, vol. 23, No. 5, May 2018) (Year: 2018).*
Patent Cooperation Treaty, International Searching Authority, Search Report and Written Opinion for PCT/US2017/067664, 10 pages, dated Mar. 8, 2018.
Suhr, O , et al., "Efficacy and safety of patisiran for familial amyloidotic polyneuropathy: a phase II multi-dose study", Orphanet Journal of Rare Diseases 10, 109 (2015).
Szebeni, J , et al., "Activation of complement by therapeutic liposomes and other lipid excipient-based therapeutic products: Prediction and prevention", Advanced Drug Delivery Reviews 63, 11020-1030 (2011).

* cited by examiner

*Primary Examiner* — Snigdha Maewall
(74) *Attorney, Agent, or Firm* — Viksnins Harris Padys Malen LLP

(57) ABSTRACT

Certain embodiments of the invention provide methods of ameliorating an infusion reaction in a mammal in need thereof.

11 Claims, 2 Drawing Sheets

METHODS FOR AMELIORATING INFUSION REACTIONS

CROSS-REFERENCE TO RELATED APPLICATION

This patent application claims the benefit of priority of U.S. application Ser. No. 62/437,537, filed Dec. 21, 2016, which application is herein incorporated by reference.

BACKGROUND

Infusion reactions may occur during and after the intravenous administration of proteins, liposomes, micelles and other natural or synthetic macromolecules, aggregates or nanoparticles, such as nanoparticles in the submicron size range. Animal studies have indicated that many of these reactions are associated with complement activation and stimulation of the innate immune system. For example, administration of lipid nanoparticles can be associated with adverse reactions, such as a temporary but substantial elevation or drop in blood pressure.

Accordingly, there is a continued unmet medical need for new compositions and methods for preventing and treating infusion reactions.

SUMMARY OF THE INVENTION

Accordingly, certain embodiments of the invention provide a method of ameliorating an infusion reaction associated with intravenous administration of at least one lipid formulated therapeutic agent in a mammal in need thereof (e.g., a human), comprising administering to the mammal via injection a therapeutically effective amount of a nonsteroidal anti-inflammatory (NSAID) prior to the at least one lipid formulated therapeutic agent being intravenously administered.

Certain embodiments of the invention provide a method of ameliorating an infusion reaction associated with intravenous administration of at least one lipid formulated therapeutic agent in a mammal in need thereof (e.g., a human), comprising administering to the mammal, in order, 1) a therapeutically effective amount of a nonsteroidal anti-inflammatory (NSAID); and 2) the at least one lipid formulated therapeutic agent, wherein the NSAID is administered via injection and the at least one lipid formulated therapeutic agent is administered intravenously.

Certain embodiments of the invention provide a method of treating an infusion reaction associated with intravenous administration of at least one lipid formulated therapeutic agent in a mammal in need thereof (e.g., a human), comprising administering to the mammal via injection a therapeutically effective amount of a nonsteroidal anti-inflammatory (NSAID) prior to the at least one lipid formulated therapeutic agent being intravenously administered.

Certain embodiments of the invention provide a method of treating an infusion reaction associated with intravenous administration of at least one lipid formulated therapeutic agent in a mammal in need thereof (e.g., a human), comprising administering to the mammal, in order, 1) a therapeutically effective amount of a nonsteroidal anti-inflammatory (NSAID); and 2) the at least one lipid formulated therapeutic agent, wherein the NSAID is administered via injection and the at least one lipid formulated therapeutic agent is administered intravenously.

Certain embodiments of the invention provide a method of treating a disease or condition in a mammal in need thereof, comprising administering to the mammal via injection a therapeutically effective amount of a nonsteroidal anti-inflammatory (NSAID) prior to at least one lipid formulated therapeutic agent being intravenously administered.

Certain embodiments of the invention provide a method of treating a disease or condition in a mammal in need thereof, comprising administering to the mammal, in order, 1) a therapeutically effective amount of a nonsteroidal anti-inflammatory (NSAID); and 2) at least one lipid formulated therapeutic agent, wherein the NSAID is administered via injection and the at least one lipid formulated therapeutic agent is administered intravenously.

Certain embodiments of the invention provide a kit comprising a nonsteroidal anti-inflammatory (NSAID) and at least one lipid formulated therapeutic agent, a container, and a package insert or label indicating the administration of the NSAID via injection prior to the intravenous administration of the at least one lipid formulated therapeutic agent, for ameliorating an infusion reaction associated with the intravenous administration of the at least one lipid formulated therapeutic agent.

Certain embodiments of the invention provide a nonsteroidal anti-inflammatory (NSAID) for use in ameliorating an infusion reaction associated with intravenous administration of at least one lipid formulated therapeutic agent in a mammal.

Certain embodiments of the invention provide the use of a nonsteroidal anti-inflammatory (NSAID) in the preparation of a medicament for ameliorating an infusion reaction associated with intravenous administration of at least one lipid formulated therapeutic agent in a mammal.

Certain embodiments of the invention provide a combination of a nonsteroidal anti-inflammatory (NSAID) and at least one lipid formulated therapeutic agent for the prophylactic or therapeutic treatment of a disease or condition.

Certain embodiments of the invention provide the use of a combination of a nonsteroidal anti-inflammatory (NSAID) and at least one lipid formulated therapeutic agent in the preparation of a medicament for the treatment of a disease or condition in a mammal.

DETAILED DESCRIPTION

Figure 1:
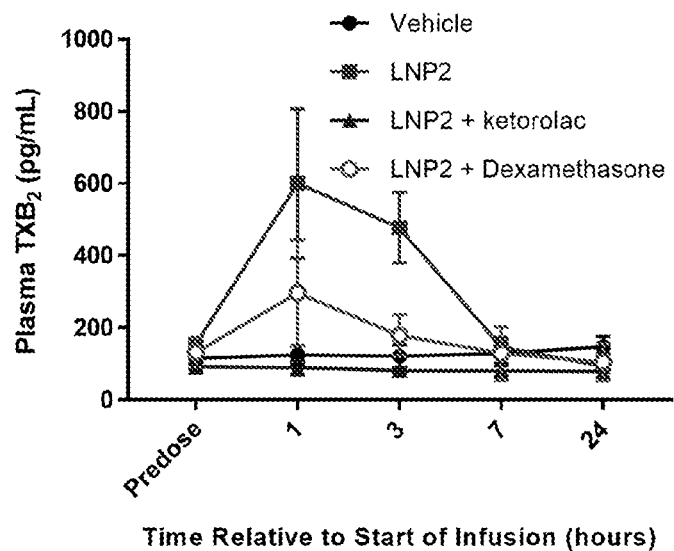
FIG. 1. The effect of LNP2 infusion (with and without ketorolac or dexamethasone) on the concentration of thromboxane B2 in plasma from mixed venous blood. Results are expressed as the mean+/−sem (n=4) at each time point.

Certain methods of the invention may be used to promote improved safety and tolerability of lipid formulated therapeutic agent(s). For example, the present invention provides methods for treating, preventing, reducing the risk or likelihood of developing (e.g., reducing the susceptibility to), and/or ameliorating an infusion reaction associated with the intravenous administration of at least one lipid formulated therapeutic agent in a mammal in need thereof (e.g., human, such as a human in need thereof), the method comprising administering to the mammal via injection a therapeutically effective amount of a nonsteroidal anti-inflammatory (NSAID) prior to the at least one lipid formulated therapeutic agent being intravenously administered.

As used herein, the term "infusion reaction" refers to a variety of symptoms which may sometimes occur during and after the intravenous administration of proteins, liposomes, micelles and other natural or synthetic macromolecules, aggregates or nanoparticles, such as lipid nanoparticles in the submicron range. Manifestations of such reactions may include, but are not limited to, tachycardia, bradycardia, dyspnea, hypotension, hypertension, chest pain, dysrhythmias, flushing, urticaria, generalized pruritis, fever, rigors and bronchospasm.

Associated laboratory abnormalities may include leukocytosis, increases in acute phase reactants and increased levels of cytokines and thromboxane B2. The reaction may be an acute reaction or may be a delayed reaction. For example, as described in the Example, acute hypertensive effects were observed within minutes of starting the infusion, whereas delayed hypotension was observed hours later (e.g., 8-9 hours after the start of the infusion). A given subject's infusion reaction may comprise a single symptom or multiple symptoms. Additionally, a subject may experience multiple episodes of a given symptom after the start of an infusion. Generally, symptoms typically subside within about 24 hours after the start of the infusion.

Accordingly, in certain embodiments of the invention the infusion reaction comprises one or more symptoms selected from tachycardia, bradycardia, dyspnea, hypotension, hypertension, chest pain and/or pressure, dysrhythmias, flushing, urticaria, generalized pruritis, fever, rigors, bronchospasm, leukocytosis, increased acute phase reactants, increased levels of cytokines and increased levels of thromboxane B2. In certain embodiments, the infusion reaction comprises hypertension and/or hypotension. In certain embodiments, the infusion reaction comprises hypertension followed by hypotension. In certain embodiments, the infusion reaction comprises an increase in plasma thromboxane B2 levels.

As used herein, the term "ameliorate" or "ameliorating" refers to preventing occurrence or recurrence of one or more symptoms of an infusion reaction, alleviation of symptoms of an infusion reaction, diminishment of any direct or indirect pathological consequences of an infusion reaction, decreasing the rate of progression of an infusion reaction, and/or lessening the severity of one or more symptoms of an infusion reaction. Methods for detecting/measuring infusion reaction symptoms are known in the art, for example, using methods described in the Example. In certain embodiments, symptoms are compared to a control mammal, such as a mammal intravenously administered a lipid formulated therapeutic agent without prior injection of a NSAID.

Certain embodiments of the invention provide methods for treating an infusion reaction associated with the intravenous administration of at least one lipid formulated therapeutic agent in a mammal in need thereof (e.g., human, such as a human in need thereof), the method comprising administering to the mammal via injection a therapeutically effective amount of a nonsteroidal anti-inflammatory (NSAID) prior to the at least one lipid formulated therapeutic agent being intravenously administered.

Certain embodiments of the invention also provide methods of treating a disease or condition in a mammal in need thereof, comprising administering to the mammal via injection a therapeutically effective amount of a nonsteroidal anti-inflammatory (NSAID) prior to at least one lipid formulated therapeutic agent being intravenously administered.

As used herein, "treatment" (and grammatical variations thereof such as "treat" or "treating") refers to clinical intervention to alter the natural course of the individual being treated, and can be performed either for prophylaxis or during the course of clinical pathology. Desirable effects of treatment include, but are not limited to, preventing occurrence or recurrence of a disease or condition, alleviation of symptoms, diminishment of any direct or indirect pathological consequences of the disease or condition, decreasing the rate of progression of the disease or condition, amelioration or palliation of the disease/condition state, and remission or improved prognosis.

In certain embodiments, the disease or condition is a Hepatitis B viral (HBV) infection. In certain embodiments, the disease or condition is a HBV and a Hepatitis D viral (HDV) infection. The term "Hepatitis B virus" (abbreviated as HBV) refers to a virus species of the genus Orthohepadnavirus, which is a part of the Hepadnaviridae family of viruses, and that is capable of causing liver inflammation in humans. The term "Hepatitis D virus" (abbreviated as HDV) refers to a virus species of the genus Deltaviridae, which is capable of causing liver inflammation in humans.

The term "nucleic acid" as used herein refers to a polymer containing at least two nucleotides (i.e., deoxyribonucleotides or ribonucleotides) in either single- or double-stranded form and includes DNA and RNA. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs and/or modified residues include, without limitation, phosphorothioates, phosphoramidates, methyl phosphonates, chiral-methyl phosphonates, 2'-O-methyl ribonucleotides, and peptide-nucleic acids (PNAs). Additionally, nucleic acids can include one or more UNA moieties.

The term "nucleic acid" includes any oligonucleotide or polynucleotide, with fragments containing up to 60 nucleotides generally termed oligonucleotides, and longer fragments termed polynucleotides. A deoxyribooligonucleotide consists of a 5-carbon sugar called deoxyribose joined covalently to phosphate at the 5' and 3' carbons of this sugar to form an alternating, unbranched polymer. DNA may be in the form of, e.g., antisense molecules, plasmid DNA, pre-condensed DNA, a PCR product, vectors, expression cassettes, chimeric sequences, chromosomal DNA, or derivatives and combinations of these groups. A ribooligonucleotide consists of a similar repeating structure where the 5-carbon sugar is ribose. RNA may be in the form, for example, of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Accordingly, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic AcidRes.*, 19:5081 (1991); Ohtsuka et al., *J. Biol. Chem.*, 260:2605-2608 (1985); Rossolini et al., *Mol. Cell. Probes*, 8:91-98 (1994)).

An "isolated" or "purified" DNA molecule or RNA molecule is a DNA molecule or RNA molecule that exists apart from its native environment. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "unlocked nucleobase analogue" (abbreviated as "UNA") refers to an acyclic nucleobase in which the C2' and C3' atoms of the ribose ring are not covalently linked. The term "unlocked nucleobase analogue" includes nucleobase analogues having the following structure identified as Structure A:

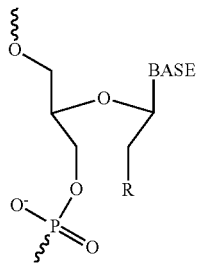

Structure A wherein R is hydroxyl, and Base is any natural or unnatural base such as, for example, adenine (A), cytosine (C), guanine (G) and thymine (T). UNA include the molecules identified as acyclic 2'-3'-seco-nucleotide monomers in U.S. Pat. No. 8,314,227.

Oligonucleotides may specifically hybridize to or may be complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

The term "small-interfering RNA" or "siRNA" as used herein refers to double stranded RNA (i.e., duplex RNA) that is capable of reducing or inhibiting the expression of a target gene or sequence (e.g., by mediating the degradation or inhibiting the translation of mRNAs which are complementary to the siRNA sequence) when the siRNA is in the same cell as the target gene or sequence. The siRNA may have substantial or complete identity to the target gene or sequence, or may comprise a region of mismatch (i.e., a mismatch motif). In certain embodiments, the siRNAs may be about 19-25 (duplex) nucleotides in length, and is preferably about 20-24, 21-22, or 21-23 (duplex) nucleotides in length. siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand.

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA,* 99:9942-9947 (2002); Calegari et al., *Proc. Natl. Acad. Sci. USA,* 99:14236 (2002); Byrom et al., *Ambion TechNotes,* 10(1):4-6 (2003); Kawasaki et al., *Nucleic Acids Res.,* 31:981-987 (2003); Knight et al., *Science,* 293:2269-2271 (2001); and Robertson et al., *J. Biol. Chem.,* 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

The phrase "inhibiting expression of a target gene" refers to the ability of a siRNA to silence, reduce, or inhibit expression of a target gene (e.g., a gene within the HBV genome). To examine the extent of gene silencing, a test sample (e.g., a biological sample from an organism of interest expressing the target gene or a sample of cells in culture expressing the target gene) is contacted with a siRNA that silences, reduces, or inhibits expression of the target gene. Expression of the target gene in the test sample is compared to expression of the target gene in a control sample (e.g., a biological sample from an organism of interest expressing the target gene or a sample of cells in culture expressing the target gene) that is not contacted with the siRNA. Control samples (e.g., samples expressing the target gene) may be assigned a value of 100%. In particular embodiments, silencing, inhibition, or reduction of expression of a target gene is achieved when the value of the test sample relative to the control sample (e.g., buffer only, an siRNA sequence that targets a different gene, a scrambled siRNA sequence, etc.) is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, or 0%. Suitable assays include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art. An "effective amount" or "therapeutically effective amount" of a therapeutic nucleic acid such as a siRNA is an amount sufficient to produce the desired effect, e.g., an inhibition of expression of a target sequence in comparison to the normal expression level detected in the absence of a siRNA. In particular embodiments, inhibition of expression of a target gene or target sequence is achieved when the value obtained with a siRNA relative to the control (e.g., buffer only, an siRNA sequence that targets a different gene, a scrambled siRNA sequence, etc.) is about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 70%, 65%, 60%, 55%, 50%, 45%, 40%, 35%, 30%, 25%, 20%, 15%, 10%, 5%, or 0%. Suitable assays for measuring the expression of a target gene or target sequence include, but are not limited to, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver a therapeutic agent (e.g., a nucleic acid, such as a siRNA) to a target site of interest (e.g., cell, tissue, organ, and the like). In preferred embodiments, the lipid particle is typically formed from a cationic lipid, a non-cationic lipid, and optionally a conjugated lipid that prevents aggregation of the particle. A lipid particle that includes a therapeutic agent is referred to as a therapeutic agent-lipid particle. A lipid particle that includes a nucleic acid molecule (e.g., siRNA molecule) is referred to as a nucleic acid-lipid particle. Typically, the nucleic acid is fully encapsulated within the lipid particle, thereby protecting the nucleic acid from enzymatic degradation.

In certain instances, nucleic acid-lipid particles are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a lipid particle as set forth in PCT Publication No. WO 00/03683, the disclosure of which is herein incorporated by reference in its entirety for all purposes.

The lipid particles typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides a therapeutic nucleic acid such as a siRNA, with full encapsulation, partial encapsulation, or both. In a preferred embodiment, the nucleic acid (e.g., siRNA) is fully encapsulated in the lipid particle (e.g., to form a nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DMA, DLin-K-C4-DMA, DLen-C2K-DMA, γ-DLen-C2K-DMA, DLin-M-C2-DMA (also known as MC2), and DLin-M-C3-DMA (also known as MC3).

The term "salts" includes any anionic and cationic complex, such as the complex formed between a cationic lipid and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

Administration of a compound as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" mean that, when substituted, at least one hydrogen atom is replaced with a substituent. In the case of an oxo substituent (=O), two hydrogen atoms are replaced. In this regard, substituents include, but are not limited to, oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^Y$, —SO$_n$R$^x$, and —SO$_n$NR$^x$R$^y$, wherein n is 0, 1, or 2, R$^x$ and R$^Y$ are the same or different and are independently hydrogen, alkyl, or heterocycle, and each of the alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^Y$, —SO$_n$R$^x$, and —SO$_n$NR$^x$R$^y$. The term "optionally substituted," when used before a list of substituents, means that each of the substituents in the list may be optionally substituted as described herein.

The term "halogen" includes fluoro, chloro, bromo, and iodo.

The term "fusogenic" refers to the ability of a lipid particle to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

The term "electron dense core", when used to describe a lipid particle, refers to the dark appearance of the interior portion of a lipid particle when visualized using cryo transmission electron microscopy ("cyroTEM"). Some lipid particles have an electron dense core and lack a lipid bilayer structure. Some lipid particles have an electron dense core, lack a lipid bilayer structure, and have an inverse Hexagonal or Cubic phase structure. While not wishing to be bound by theory, it is thought that the non-bilayer lipid packing provides a 3-dimensional network of lipid cylinders with water and nucleic acid on the inside, i.e., essentially a lipid droplet interpenetrated with aqueous channels containing the nucleic acid.

"Distal site," as used herein, refers to a physically separated site, which is not limited to an adjacent capillary bed, but includes sites broadly distributed throughout an organism.

"Serum-stable" in relation to nucleic acid-lipid particles means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as a siRNA within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as a siRNA directly to a target site within an organism. For example, an agent can be locally delivered by direct injection into a disease site, other target site, or a target organ such as the liver, heart, pancreas, kidney, and the like.

The term "virus particle load", as used herein, refers to a measure of the number of virus particles (e.g., HBV and/or HDV) present in a bodily fluid, such as blood. For example, particle load may be expressed as the number of virus particles per milliliter of, e.g., blood. Particle load testing may be performed using nucleic acid amplification based tests, as well as non-nucleic acid-based tests (see, e.g., Puren et al., The Journal of Infectious Diseases, 201:S27-36 (2010)).

The term "mammal" refers to any mammalian species such as a human, mouse, rat, dog, cat, hamster, guinea pig, rabbit, livestock, and the like.

Nonsteroidal Anti-Inflammatory Drugs (NSAIDs)

As discussed herein, certain embodiments of the invention provide methods for ameliorating an infusion reaction associated with intravenous administration of at least one lipid formulated therapeutic agent in a mammal in need thereof (e.g., a human subject), comprising administering to the mammal via injection a therapeutically effective amount of a nonsteroidal anti-inflammatory (NSAID) prior to the at least one lipid formulated therapeutic agent being intravenously administered.

NSAIDs are a drug class that provide analgesic (pain-killing) and antipyretic (fever-reducing) effects, and, in higher doses, anti-inflammatory effects. The term nonsteroidal distinguishes these drugs from steroids, which, among a broad range of other effects, have a similar eicosanoid-depressing, anti-inflammatory action. Typically, NSAIDs inhibit the activity of cyclooxygenase-1 (COX-1) and cyclooxygenase-2 (COX-2), and thereby the synthesis of prostaglandins and thromboxanes.

NSAIDs include for example, but are not limited to, aspirin (acetylsalicylic acid), diflunisal, salicylic acid, salicylates, salsalate, ibuprofen, dexibuprofen, naproxen, fenoprofen, ketoprofen, dexketoprofen, fluibiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, phenylbutazone, mefenamic acid, meclofenamic acid, flufenamic acid, tolfenamic acid, celecoxib, rofecoxib, valdecoxib, parecoxib, lumiracoxib, etoricoxib, firocoxib, nimesulide, clonixin, licofelone, flunixin meglumin and H-harpagide.

In certain embodiments, the NSAID is a NSAID that is capable of being administered via injection (e.g., parenterally, such as intravenously, intramuscularly or subcutaneously). In certain embodiments, the NSAID is a NSAID that is capable of being administered parenterally. In certain embodiments, the NSAID is a NSAID that is capable of being administered intravenously. In certain embodiments, the NSAID is a NSAID discussed in Pain Medicine, 2013; 14:S11-S17, which is incorporated by reference in its entirety herein.

In certain embodiments, the NSAID is selected from the group consisting of indomethacin, ketorolac, ibuprofen, diclofenac, lornoxicam, parecoxib, tenoxicam, phenylbutazone and flunixin meglumin. In certain embodiments, the NSAID is selected from the group consisting of indomethacin, ketorolac, ibuprofen, diclofenac, lornoxicam, parecoxib, tenoxicam. In certain embodiments, the NSAID is selected from the group consisting of indomethacin, ketorolac and ibuprofen. In certain embodiments, the NSAID is ketorolac. In certain embodiments, the NSAID is indomethacin. In certain embodiments, the NSAID is ibuprofen.

As discussed herein, the NSAID is generally administered via injection. Accordingly, in certain embodiments, the NSAID is administered parenterally. In certain embodiments, the NSAID is administered intravenously. In certain embodiments, the NSAID is administered intramuscularly. In certain embodiments, the NSAID is administered subcutaneously.

Therapeutic Agents

As discussed herein, injection of a NSAID prior to intravenous administration of at least one lipid formulated therapeutic agent may ameliorate an infusion reaction. Accordingly, in certain embodiments, the therapeutic agent is an agent that is capable of being formulated in a lipid (e.g., in a lipid nanoparticle formulation (LNP)).

Additionally, certain embodiments of the invention also provide for the administration of one or more additional therapeutic agents (i.e., a second, third, fourth, etc. therapeutic agent), which may or may not be lipid formulated. In certain embodiments, the one or more additional therapeutic agents are administered sequentially or simultaneously with the NSAID or the lipid formulated therapeutic agent. For example, in certain embodiments, dexamethasone may be administered sequentially or simultaneously with the NSAID.

Thus, the therapeutic agent (i.e., the lipid formulated therapeutic agent or the additional therapeutic agent) may be of natural or synthetic origin. For example, it may be a nucleic acid, a polypeptide, a protein, a peptide, or an organic compound. In certain embodiments, the therapeutic agent is a nucleic acid, a polypeptide or an organic compound. In one embodiment, the therapeutic agent is a siRNA, mRNA, a small molecule or an antibody.

In certain embodiments, the therapeutic agent is a polypeptide, for example, an antibody, or a fragment or derivative thereof, such as a Fab fragment, a CDR region, or a single chain antibody. In certain embodiments, the therapeutic agent is an anti-PD-1 antibody, or fragment thereof.

In certain embodiments, the therapeutic agent is a small molecule. The term "small molecule" includes organic molecules having a molecular weight of less than about 1000 amu. In one embodiment a small molecule can have a molecular weight of less than about 800 amu. In another embodiment a small molecule can have a molecular weight of less than about 500 amu. In certain embodiments, the therapeutic agent is a steroid (e.g., dexamethasone). In certain embodiments the therapeutic agent is a NSAID (e.g., a NSAID described herein), which may be the same or different from the NSAID administered via injection.

In certain embodiments, the therapeutic agent is a nucleic acid. In certain embodiments, the nucleic acid is mRNA. In certain embodiments, the nucleic acid is an antisense nucleic acid (e.g., siRNA or shRNA) capable of inhibiting transcription or translation of the corresponding messenger RNA (mRNA). In certain embodiments, the nucleic acid is siRNA.

siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Typically, siRNA are chemically synthesized. The oligonucleotides that comprise the siRNA molecules can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol. Alternatively, syntheses at the 0.2 µmol scale can be performed on a 96-well plate synthesizer from Protogene (Palo Alto, Calif.). However, a larger or smaller scale of synthesis is also within the scope. Suitable reagents for oligonucleotide synthesis, methods for RNA deprotection, and methods for RNA purification are known to those of skill in the art.

siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection.

In certain embodiments, the therapeutic agent is selected from the group consisting of:
a) reverse transcriptase inhibitors;
b) capsid inhibitors;
c) cccDNA formation inhibitors;
d) sAg secretion inhibitors;
e) oligomeric nucleotides targeted to the Hepatitis B genome; and
f) immunostimulators.

Reverse Transcriptase Inhibitors

In certain embodiments, the reverse transcriptase inhibitor is a nucleoside analog.

In certain embodiments, the reverse transcriptase inhibitor is a nucleoside analog reverse-transcriptase inhibitor (NARTI or NRTI).

In certain embodiments, the reverse transcriptase inhibitor is a nucleotide analog reverse-transcriptase inhibitor (NtARTI or NtRTI).

The term reverse transcriptase inhibitor includes, but is not limited to: entecavir, clevudine, telbivudine, lamivudine, adefovir, tenofovir, tenofovir disoproxil, tenofovir alafenamide, adefovir dipovoxil, (1R,2R,3R,5R)-3-(6-amino-9H-9-purinyl)-2-fluoro-5-(hydroxymethyl)-4-methylenecyclopentan-1-ol (described in U.S. Pat. No. 8,816,074), emtricitabine, abacavir, elvucitabine, ganciclovir, lobucavir, famciclovir, penciclovir, and amdoxovir.

The term reverse transcriptase inhibitor includes, but is not limited to, entecavir, lamivudine, and (1R,2R,3R,5R)-3-(6-amino-9H-9-purinyl)-2-fluoro-5-(hydroxymethyl)-4-methylenecyclopentan-1-ol.

The term reverse transcriptase inhibitor includes, but is not limited to a covalently bound phosphoramidate or phosphonamidate moiety of the above-mentioned reverse transcriptase inhibitors, or as described in, for example, U.S. Pat. No. 8,816,074, US 2011/0245484 A1, and US 2008/0286230A1.

The term reverse transcriptase inhibitor includes, but is not limited to, nucleotide analogs that comprise a phosphoramidate moiety, such as, methyl (((((1R,3R,4R,5R)-3-(6-amino-9H-purin-9-yl)-4-fluoro-5-hydroxy-2-methylenecyclopentyl)methoxy)(phenoxy)phosphoryl)-(D or L)-alaninate and methyl (((((1R,2R,3R,4R)-3-fluoro-2-hydroxy-5-methylene-4-(6-oxo-1,6-dihydro-9H-purin-9-yl)cyclopentyl)methoxy)(phenoxy)phosphoryl)-(D or L)-alaninate. Also included are the individual diastereomers thereof, which includes, for example, methyl ((R)-(((1R,3R,4R,5R)-3-(6-amino-9H-purin-9-yl)-4-fluoro-5-hydroxy-2-methylenecyclopentyl)methoxy)(phenoxy)phosphoryl)-(D or L)-alaninate and methyl ((S)-(((1R,3R,4R,5R)-3-(6-amino-9H-purin-9-yl)-4-fluoro-5-hydroxy-2-methylenecyclopentyl)methoxy)(phenoxy)phosphoryl)-(D or L)-alaninate.

The term reverse transcriptase inhibitor includes, but is not limited to a phosphonamidate moiety, such as, tenofovir alafenamide, as well as those described in US 2008/0286230 A1. Methods for preparing stereoselective phosphoramidate or phosphonamidate containing actives are described in, for example, U.S. Pat. No. 8,816,074, as well as US 2011/0245484 A1 and US 2008/0286230 A1.

Capsid Inhibitors

As described herein the term "capsid inhibitor" includes compounds that are capable of inhibiting the expression and/or function of a capsid protein either directly or indirectly. For example, a capsid inhibitor may include, but is not limited to, any compound that inhibits capsid assembly, induces formation of non-capsid polymers, promotes excess capsid assembly or misdirected capsid assembly, affects capsid stabilization, and/or inhibits encapsidation of RNA. Capsid inhibitors also include any compound that inhibits capsid function in a downstream event(s) within the replication process (e.g., viral DNA synthesis, transport of relaxed circular DNA (rcDNA) into the nucleus, covalently closed circular DNA (cccDNA) formation, virus maturation, budding and/or release, and the like). For example, in certain embodiments, the inhibitor detectably inhibits the expression level or biological activity of the capsid protein as measured, e.g., using an assay described herein. In certain embodiments, the inhibitor inhibits the level of rcDNA and downstream products of viral life cycle by at least 5%, at least 10%, at least 20%, at least 50%, at least 75%, or at least 90%.

The term capsid inhibitor includes compounds described in International Patent Applications Publication Numbers WO2013006394, WO2014106019, and WO2014089296, including the following compounds:

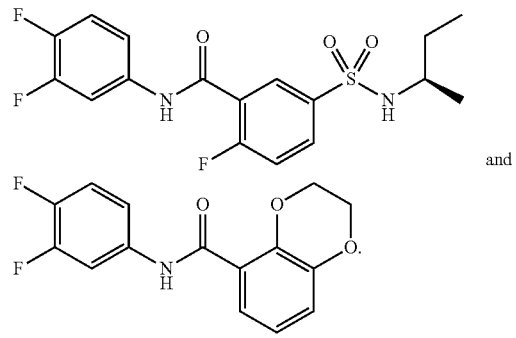

and

The term capsid inhibitor also includes the compounds Bay-41-4109 (see International Patent Application Publication Number WO/2013/144129), AT-61 (see International Patent Application Publication Number WO/1998/33501; and King, R W, et al., Antimicrob Agents Chemother, 1998, 42, 12, 3179-3186), DVR-O1 and DVR-23 (see International Patent Application Publication Number WO 2013/006394; and Campagna, M R, et al., J. of Virology, 2013, 87, 12, 6931, and pharmaceutically acceptable salts thereof:

Bay-41-4109

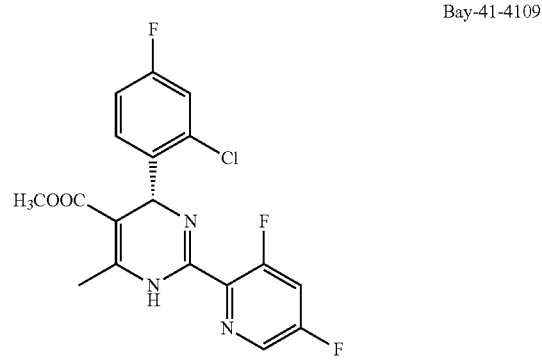

AT-61

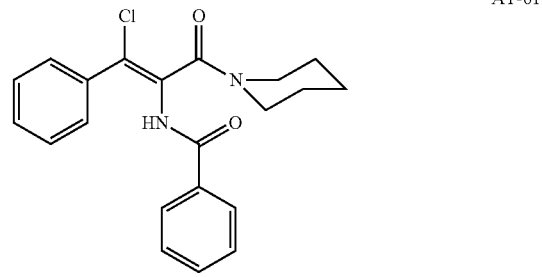

DVR-01

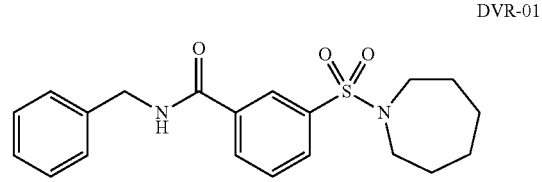

DVR-23

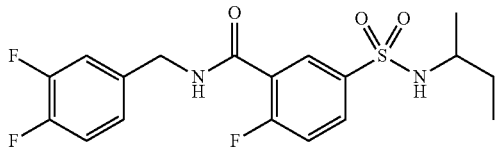

cccDNA Formation Inhibitors

Covalently closed circular DNA (cccDNA) is generated in the cell nucleus from viral rcDNA and serves as the transcription template for viral mRNAs. As described herein, the term "cccDNA formation inhibitor" includes compounds that are capable of inhibiting the formation and/or stability of cccDNA either directly or indirectly. For example, a cccDNA formation inhibitor may include, but is not limited to, any compound that inhibits capsid disassembly, rcDNA entry into the nucleus, and/or the conversion of rcDNA into cccDNA. For example, in certain embodiments, the inhibitor detectably inhibits the formation and/or stability of the cccDNA as measured, e.g., using an assay described herein. In certain embodiments, the inhibitor inhibits the formation and/or stability of cccDNA by at least 5%, at least 10%, at least 20%, at least 50%, at least 75%, or at least 90%.

The term cccDNA formation inhibitor includes compounds described in International Patent Application Publication Number WO2013130703, including the following compounds:

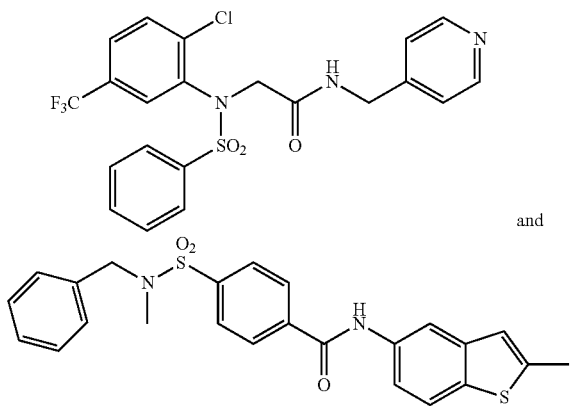

and

The term cccDNA formation inhibitor includes, but is not limited to those generally and specifically described in United States Patent Application Publication Number US 2015/0038515 A1. The term cccDNA formation inhibitor includes, but is not limited to, 1-(phenylsulfonyl)-N-(pyridin-4-ylmethyl)-1H-indole-2-carboxamide; 1-Benzenesulfonyl-pyrroli dine-2-carboxylic acid (pyridin-4-ylmethyl)-amide; 2-(2-chloro-N-(2-chloro-5-(trifluoromethyl)phenyl)-4-(trifluoromethyl)phenylsulfonamido)-N-(pyridin-4-ylmethyl)acetamide; 2-(4-chloro-N-(2-chloro-5-(trifluoromethyl)phenyl)phenylsulfonamido)-N-(pyridin-4-ylmethyl)acetamide; 2-(N-(2-chloro-5-(trifluoromethyl)phenyl)-4-(trifluoromethyl)phenylsulfonamido)-N-(pyridin-4-ylmethyl)acetamide; 2-(N-(2-chloro-5-(trifluoromethyl)phenyl)-4-methoxyphenylsulfonamido)-N-(pyridin-4-ylmethyl)acetamide; 2-(N-(2-chloro-5-(trifluoromethyl)phenyl)phenylsulfonamido)-N-((1-methylpiperidin-4-yl)methyl)acetamide; 2-(N-(2-chloro-5-(trifluoromethyl) phenyl)phenylsulfonamido)-N-(piperidin-4-ylmethyl) acetamide; 2-(N-(2-chloro-5-(trifluoromethyl)phenyl) phenylsulfonamido)-N-(pyridin-4-ylmethyl)propanamide; 2-(N-(2-chloro-5-(trifluoromethyl)phenyl)phenylsulfonamido)-N-(pyridin-3-ylmethyl)acetamide; 2-(N-(2-chloro-5-(trifluoromethyl)phenyl)phenyl sulfonamido)-N-(pyrimidin-5-ylmethyl)acetamide; 2-(N-(2-chloro-5-(trifluoromethyl)phenyl)phenylsulfonamido)-N-(pyrimidin-4-ylmethyl)acetamide; 2-(N-(5-chloro-2-fluorophenyl) phenylsulfonamido)-N-(pyridin-4-ylmethyl)acetamide; 2-[(2-chloro-5-trifluoromethyl-phenyl)-(4-fluoro-benzenesulfonyl)-amino]-N-pyridin-4-ylmethyl-acetamide; 2-[(2-chloro-5-trifluoromethyl-phenyl)-(toluene-4-sulfonyl)-amino]-N-pyridin-4-ylmethyl-acetamide; 2-[benzenesulfonyl-(2-bromo-5-trifluoromethyl-phenyl)-amino]-N-pyridin-4-ylmethyl-acetamide; 2-[benzenesulfonyl-(2-chloro-5-trifluoromethyl-phenyl)-amino]-N-(2-methyl-benzothiazol-5-yl)-acetamide; 2-[benzenesulfonyl-(2-chloro-5-trifluoromethyl-phenyl)-amino]-N-[4-(4-methyl-piperazin-1-yl)-benzyl]-acetamide; 2-[benzenesulfonyl-(2-chloro-5-trifluoromethyl-phenyl)-amino]-N-[3-(4-methyl-piperazin-1-yl)-benzyl]-acetamide; 2-[benzenesulfonyl-(2-chloro-5-trifluoromethyl-phenyl)-amino]-N-benzyl-acetamide; 2-[benzenesulfonyl-(2-chloro-5-trifluoromethyl-phenyl)-amino]-N-pyridin-4-ylmethyl-acetamide; 2-[benzenesulfonyl-(2-chloro-5-trifluoromethyl-phenyl)-amino]-N-pyridin-4-ylmethyl-propionamide; 2-[benzenesulfonyl-(2-fluoro-5-trifluoromethyl-phenyl)-amino]-N-pyridin-4-ylmethyl-acetamide; 4 N-(2-chloro-5-(trifluoromethyl)phenyl)phenyl sulfonamido)-N-(pyridin-4-yl-methyl)butanamide; 4-((2-(N-(2-chloro-5-(trifluoromethyl)phenyl)phenylsulfonamido)-acetamido)-methyl)-1,1-dimethylpiperidin-1-ium chloride; 4-(benzyl-methyl-sulfamoyl)-N-(2-chloro-5-trifluoromethyl-phenyl)-benzamide; 4-(benzyl-methyl-sulfamoyl)-N-(2-methyl-1H-indol-5-yl)-benzamide; 4-(benzyl-methyl-sulfamoyl)-N-(2-methyl-1H-indol-5-yl)-benzamide; 4-(benzyl-methyl-sulfamoyl)-N-(2-methyl-benzothiazol-5-yl)-benzamide; 4-(benzyl-methyl-sulfamoyl)-N-(2-methyl-benzothiazol-6-yl)-benzamide; 4-(benzyl-methyl-sulfamoyl)-N-(2-methyl-benzothiazol-6-yl)-benzamide; 4-(benzyl-methyl-sulfamoyl)-N-pyridin-4-ylmethyl-benzamide; N-(2-aminoethyl)-2-(N-(2-chloro-5-(trifluoromethyl)phenyl) phenylsulfonamido)-acetamide; N-(2-chloro-5-(trifluoromethyl)phenyl)-N-(2-(3,4-dihydro-2,6-naphthyridin-2(1H)-yl)-2-oxoethyl)benzenesulfonamide; N-benzothiazol-6-yl-4-(benzyl-methyl-sulfamoyl)-benzamide; N-benzothiazol-6-yl-4-(benzyl-methyl-sulfamoyl)-benzamide; tert-butyl (2-(2-(N-(2-chloro-5-(trifluoromethyl)phenyl)phenylsulfonamido)acetamido)-ethyl) carbamate; and tert-butyl 4-((2-(N-(2-chloro-5-(trifluoromethyl)phenyl)phenylsulfonamido)-acetamido)-methyl)piperidine-1-carboxylate, and optionally, combinations thereof.

sAg Secretion Inhibitors

As described herein the term "sAg secretion inhibitor" includes compounds that are capable of inhibiting, either directly or indirectly, the secretion of sAg (S, M and/or L surface antigens) bearing subviral particles and/or DNA containing viral particles from HBV-infected cells. For example, in certain embodiments, the inhibitor detectably inhibits the secretion of sAg as measured, e.g., using assays known in the art or described herein, e.g., ELISA assay or by Western Blot. In certain embodiments, the inhibitor inhibits the secretion of sAg by at least 5%, at least 10%, at least 20%, at least 50%, at least 75%, or at least 90%. In certain embodiments, the inhibitor reduces serum levels of sAg in a patient by at least 5%, at least 10%, at least 20%, at least 50%, at least 75%, or at least 90%.

The term sAg secretion inhibitor includes compounds described in U.S. Pat. No. 8,921,381, as well as compounds described in United States Patent Application Publication Numbers 2015/0087659 and 2013/0303552. For example, the term includes the compounds PBHBV-001 and PBHBV-2-15, and pharmaceutically acceptable salts thereof:

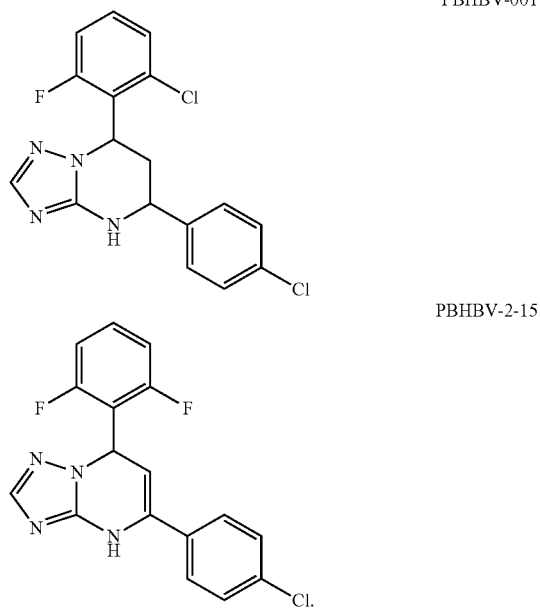

Immunostimulators

The term "immunostimulator" includes compounds that are capable of modulating an immune response (e.g., stimulate an immune response (e.g., an adjuvant)). The term immunostimulators includes polyinosinic:polycytidylic acid (poly I:C) and interferons.

The term immunostimulators includes agonists of stimulator of IFN genes (STING) and interleukins. The term also includes HBsAg release inhibitors, TLR-7 agonists (GS-9620, RG-7795), T-cell stimulators (GS-4774), RIG-1 inhibitors (SB-9200), and SMAC-mimetics (Birinapant).

Oligomeric Nucleotides

The term oligomeric nucleotide targeted to the Hepatitis B genome includes Arrowhead-ARC-520 (see U.S. Pat. No. 8,809,293; and Wooddell C I, et al., *Molecular Therapy*, 2013, 21, 5, 973-985).

The oligomeric nucleotides can be designed to target one or more genes and/or transcripts of the HBV genome.

The term oligomeric nucleotide targeted to the Hepatitis B genome also includes isolated, double stranded, siRNA molecules, that each include a sense strand and an antisense strand that is hybridized to the sense strand. The siRNA target one or more genes and/or transcripts of the HBV genome.

Carrier Systems Containing a Therapeutic Agent

Lipid Particles

In certain embodiments of the invention the at least one lipid formulated therapeutic agent is formulated in a lipid nanoparticle (LNP) comprising the at least one therapeutic agent, a cationic lipid and a non-cationic lipid. In certain embodiments, the LNP further comprises a conjugated lipid that inhibits aggregation of particles. In one embodiment, the lipid particles can comprise one or more therapeutic agents (e.g., a nucleic acid, such as a siRNA or mRNA), a cationic lipid, a non-cationic lipid, and a conjugated lipid that inhibits aggregation of particles. In some embodiments, the therapeutic agent is fully encapsulated within the lipid portion of the lipid particle. For example, in certain embodiments, the therapeutic agent is a nucleic acid that is fully encapsulated within the lipid portion of the lipid particle such that the nucleic acid in the lipid particle is resistant in aqueous solution to nuclease degradation. In other embodiments, the lipid particles described herein are substantially non-toxic to mammals such as humans. The lipid particles typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. In certain embodiments, the lipid particles have a median diameter of from about 30 nm to about 150 nm. The lipid particles also typically have a lipid:therapeutic agent ratio (e.g., a lipid:nucleic acid ratio) (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1. In certain embodiments, the therapeutic agent-lipid particle has a lipid:therapeutic agent mass ratio of from about 5:1 to about 15:1. In certain embodiments, the therapeutic agent is a nucleic acid and the nucleic acid-lipid particle has a lipid:nucleic acid (e.g., siRNA) mass ratio of from about 5:1 to about 15:1.

In certain embodiments, the therapeutic agent is a nucleic acid. Accordingly, certain embodiments of the invention include serum-stable nucleic acid-lipid particles which comprise one or more siRNA or mRNA molecules, a cationic lipid (e.g., one or more cationic lipids of Formula I-III or salts thereof as set forth herein), a non-cationic lipid (e.g., mixtures of one or more phospholipids and cholesterol), and a conjugated lipid that inhibits aggregation of the particles (e.g., one or more PEG-lipid conjugates). The lipid particle may comprise at least 1, 2, 3, 4, 5, 6, 7, 8, 9, 10, or more siRNA molecules that target a gene of interest (e.g., a HBV gene) or mRNA molecules. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles, the one or more nucleic acid molecules (e.g., an siRNA molecule or mRNA molecule) may be fully encapsulated within the lipid portion of the particle, thereby protecting the siRNA from nuclease degradation. In certain instances, the nucleic acid in the nucleic acid-lipid particle is not substantially degraded after exposure of the particle to a nuclease at 37° C. for at least about 20, 30, 45, or 60 minutes. In certain other instances, the nucleic acid in the nucleic acid-lipid particle is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations is that the nucleic acid-lipid particle compositions are substantially non-toxic to mammals such as humans.

The term "fully encapsulated" indicates that the nucleic acid (e.g., a siRNA molecule or mRNA molecule) in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where $I$ and $I_o$ refer to the fluorescence intensities before and after the addition of detergent (see, Wheeler et al., *Gene Ther.*, 6:271-281 (1999)).

In some instances, the nucleic acid-lipid particle composition comprises a nucleic acid molecule (e.g., a siRNA molecule or mRNA molecule) that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the nucleic acid encapsulated therein.

In other instances, the nucleic acid-lipid particle composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input nucleic acid is encapsulated in the particles.

Depending on the intended use of the lipid particles, the proportions of the components can be varied and the delivery efficiency of a particular formulation can be measured using, e.g., an endosomal release parameter (ERP) assay.

Cationic Lipids

Any of a variety of cationic lipids or salts thereof may be used in the lipid particles either alone or in combination with one or more other cationic lipid species or non-cationic lipid species. The cationic lipids include the (R) and/or (S) enantiomers thereof.

In one aspect, the cationic lipid is a dialkyl lipid. For example, dialkyl lipids may include lipids that comprise two saturated or unsaturated alkyl chains, wherein each of the alkyl chains may be substituted or unsubstituted. In certain embodiments, each of the two alkyl chains comprise at least, e.g., 8 carbon atoms, 10 carbon atoms, 12 carbon atoms, 14 carbon atoms, 16 carbon atoms, 18 carbon atoms, 20 carbon atoms, 22 carbon atoms or 24 carbon atoms.

In one aspect, the cationic lipid is a trialkyl lipid. For example, trialkyl lipids may include lipids that comprise three saturated or unsaturated alkyl chains, wherein each of the alkyl chains may be substituted or unsubstituted. In certain embodiments, each of the three alkyl chains comprise at least, e.g., 8 carbon atoms, 10 carbon atoms, 12 carbon atoms, 14 carbon atoms, 16 carbon atoms, 18 carbon atoms, 20 carbon atoms, 22 carbon atoms or 24 carbon atoms.

In one aspect, cationic lipids of Formula I having the following structure are useful:

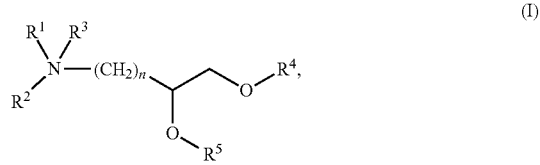

(I)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine; $R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least two sites of unsaturation; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In one preferred embodiment, $R^1$ and $R^2$ are both methyl groups. In other preferred embodiments, n is 1 or 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, wherein at least one of $R^4$ and $R^5$ comprises at least two sites of unsaturation.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, an arachidonyl moiety, and a docosahexaenoyl moiety, as well as acyl derivatives thereof (e.g., linoleoyl, linolenoyl, γ-linolenoyl, etc.). In some instances, one of $R^4$ and $R^5$ comprises a branched alkyl group (e.g., a phytanyl moiety) or an acyl derivative thereof (e.g., a phytanoyl moiety). In certain instances, the octadecadienyl moiety is a linoleyl moiety. In certain other instances, the octadecatrienyl moiety is a linolenyl moiety or a γ-linolenyl moiety. In certain embodiments, $R^4$ and $R^5$ are both linoleyl moieties, linolenyl moieties, or γ-linolenyl moieties. In particular embodiments, the cationic lipid of Formula I is 1,2-dilinoleyloxy-N,N-dimethylaminopropane (DLinDMA), 1,2-dilinolenyloxy-N,N-dimethylaminopropane (DLenDMA), 1,2-dilinoleyloxy-(N,N-dimethyl)-butyl-4-amine (C2-DLinDMA), 1,2-dilinoleoyloxy-(N,N-dimethyl)-butyl-4-amine (C2-DLinDAP), or mixtures thereof.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

The synthesis of cationic lipids such as DLinDMA and DLenDMA, as well as additional cationic lipids, is described in U.S. Patent Publication No. 20060083780, the disclosure of which is herein incorporated by reference in its entirety for all purposes. The synthesis of cationic lipids such as C2-DLinDMA and C2-DLinDAP, as well as additional cationic lipids, is described in international patent application number WO2011/000106 the disclosure of which is herein incorporated by reference in its entirety for all purposes.

In another aspect, cationic lipids of Formula II having the following structure (or salts thereof) are useful:

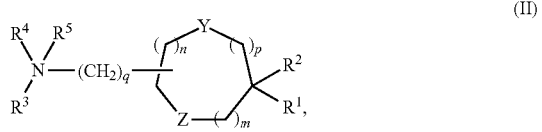

(II)

heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH. In a preferred embodiment, q is 2.

In some embodiments, the cationic lipid of Formula II is 2,2-dilinoleyl-4-(2-dimethylaminoethyl)-[1,3]-dioxolane (DLin-K-C2-DMA; "XTC2" or "C2K"), 2,2-dilinoleyl-4-(3-dimethylaminopropyl)-[1,3]-dioxolane (DLin-K-C3-DMA; "C₃K"), 2,2-dilinoleyl-4-(4-dimethylaminobutyl)-[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 2,2-dioleoyl-4-dimethylaminomethyl-[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.Cl), 2,2-dilinoleyl-4,5-bis(dimethylaminomethyl)-[1,3]-dioxolane (DLin-$K^2$-DMA), 2,2-dilinoleyl-4-methylpiperzine-[1,3]-dioxolane (D-Lin-K-N-methylpiperzine), or mixtures thereof. In one embodiment the cationic lipid of Formula II is DLin-K-C2-DMA.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

The synthesis of cationic lipids such as DLin-K-DMA, as well as additional cationic lipids, is described in PCT Publication No. WO 09/086558, the disclosure of which is herein incorporated by reference in its entirety for all purposes. The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.C1, DLin-$K^2$-DMA, and D-Lin-K-N-methylpiperzine, as well as additional cationic lipids, is described in PCT Application No. PCT/US2009/060251, entitled "Improved Amino Lipids and Methods for the Delivery of Nucleic Acids," filed Oct. 9, 2009, the disclosure of which is incorporated herein by reference in its entirety for all purposes.

In a further aspect, cationic lipids of Formula III having the following structure are useful:

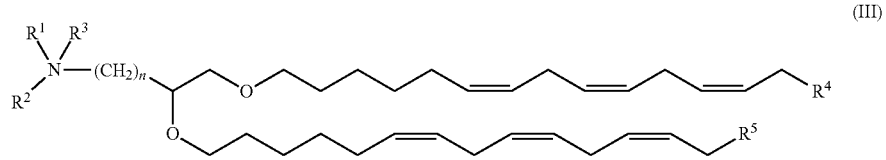

(III)

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof, $R^3$ is either absent or is hydrogen (H) or a $C_1$-$C_6$ alkyl to provide a quaternary amine; $R^4$ and $R^5$ are either absent or present and when present are either the same or different and are independently an optionally substituted $C_1$-$C_{10}$ alkyl or $C_2$-$C_{10}$ alkenyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, $R^4$ and $R^5$ are both butyl groups. In yet another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_2$-$C_6$ or $C_2$-$C_4$ alkyl or $C_2$-$C_6$ or $C_2$-$C_4$ alkenyl.

In an alternative embodiment, the cationic lipid of Formula III comprises ester linkages between the amino head group and one or both of the alkyl chains. In some embodiments, the cationic lipid of Formula III forms a salt (preferably a crystalline salt) with one or more anions. In one particular embodiment, the cationic lipid of Formula III is the oxalate (e.g., hemioxalate) salt thereof, which is preferably a crystalline salt.

Although each of the alkyl chains in Formula III contains cis double bonds at positions 6, 9, and 12 (i.e., cis,cis,cis-$\Delta^6,\Delta^9,\Delta^{12}$), in an alternative embodiment, one, two, or three of these double bonds in one or both alkyl chains may be in the trans configuration.

In a particular embodiment, the cationic lipid of Formula III has the structure:

distearyl-N,N-dimethylammonium bromide (DDAB), N-(1-(2,3-dioleoyloxy)propyl)-N,N,N-trimethylammonium chloride (DOTAP), 3-(N-(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido) ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-(5'-(cholest-5-en-3-beta-oxy)-3'-oxapentoxy)-3-dimethy-1-(cis, cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride

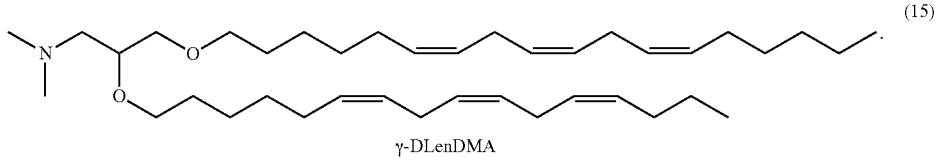

(15)

γ-DLenDMA

The synthesis of cationic lipids such as γ-DLenDMA (15), as well as additional cationic lipids, is described in U.S. Provisional Application No. 61/222,462, entitled "Improved Cationic Lipids and Methods for the Delivery of Nucleic Acids," filed Jul. 1, 2009, the disclosure of which is herein incorporated by reference in its entirety for all purposes.

The synthesis of cationic lipids such as DLin-M-C3-DMA ("MC3"), as well as additional cationic lipids (e.g., certain analogs of MC3), is described in U.S. Provisional Application No. 61/185,800, entitled "Novel Lipids and Compositions for the Delivery of Therapeutics," filed Jun. 10, 2009, and U.S. Provisional Application No. 61/287,995, entitled "Methods and Compositions for Delivery of Nucleic Acids," filed Dec. 18, 2009, the disclosures of which are herein incorporated by reference in their entirety for all purposes.

Examples of other cationic lipids or salts thereof which may be included in the lipid particles include, but are not limited to, cationic lipids such as those described in WO2011/000106, the disclosure of which is herein incorporated by reference in its entirety for all purposes, as well as cationic lipids such as N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-

(DOTAP.Cl), dilinoleylmethyl-3-dimethylaminopropionate (DLin-M-C2-DMA; also known as DLin-M-K-DMA or DLin-M-DMA), and mixtures thereof. Additional cationic lipids or salts thereof which may be included in the lipid particles are described in U.S. Patent Publication No. 20090023673, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes. The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086558, the disclosure of which is herein incorporated by reference in its entirety for all purposes. The synthesis of cationic lipids such as DO-C-DAP, DMDAP, DOTAP.Cl, DLin-M-C2-DMA, as well as additional cationic lipids, is described in PCT Application No. PCT/US2009/060251, entitled "Improved Amino Lipids and Methods for the Delivery of Nucleic Acids," filed Oct. 9, 2009, the disclosure of which is incorporated herein by reference in its entirety for all purposes. The synthesis of a number of other cationic lipids and related analogs has been described in U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from Invitrogen); LIPOFECTAMINE® (including DOSPA and DOPE, available from Invitrogen); and TRANSFECTAM® (including DOGS, available from Promega Corp.).

In some embodiments, the cationic lipid comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol %, or from about 55 mol % to about 70 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof) of the total lipid present in the particle.

In other embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

It should be understood that the percentage of cationic lipid present in the lipid particles is a target amount, and that the actual amount of cationic lipid present in the formulation may vary, for example, by ±5 mol %. For example, in one exemplary lipid particle formulation, the target amount of cationic lipid is 57.1 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle; however, one skilled in the art will understand that the total mol % may deviate slightly from 100% due to rounding, for example, 99.9 mol % or 100.1 mol %).

Further examples of cationic lipids useful for inclusion in lipid particles are shown below:

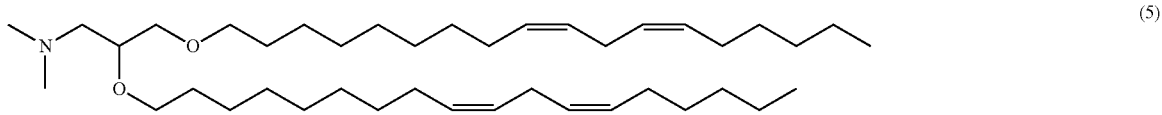

N,N-dimethyl-2,3-bis((9Z, 12Z)-octadeca-9,12-dienyloxy)propan-1-amine (5)

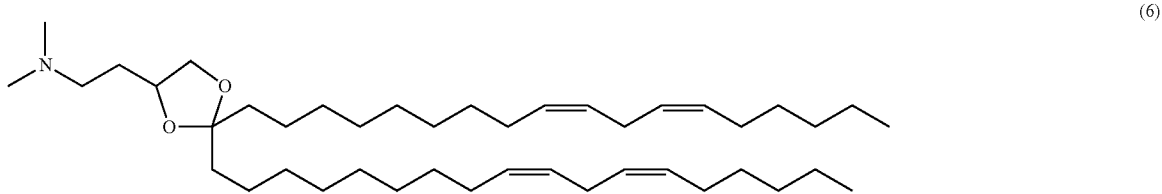

2-(2,2-di((9Z, 12Z)-octadeca-9,12-dienyl)-1,3-dioxolan-4-yl)-N,N-dimethylethanamine (6)

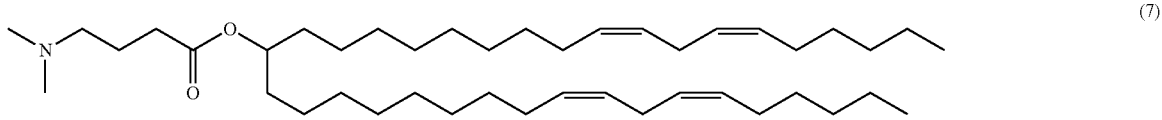

(6Z, 9Z, 28Z, 31Z)-heptatriaconta-6,9,28,31-tetraen-19-yl 4-(dimethylamino)butanoate (7)

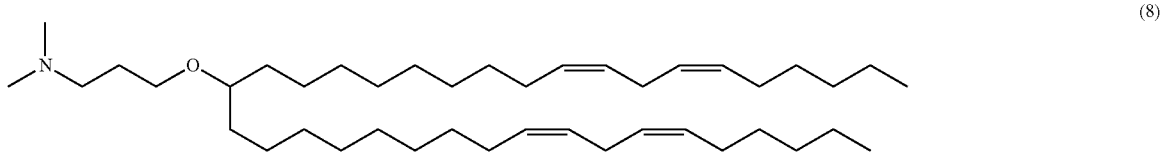

3-((6Z, 9Z, 28Z, 31Z)-heptatriaconta-6,9,28,31-tetraen-19-yloxy)-N,N-dimethylpropan-1-amine (8)

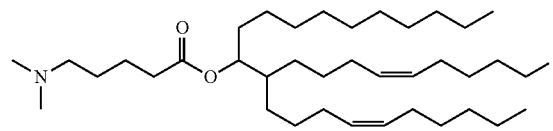

(Z)-12-((Z)-dec-4-enyl)docos-16-en-11-yl 5-(dimethylamino)pentanoate (53)

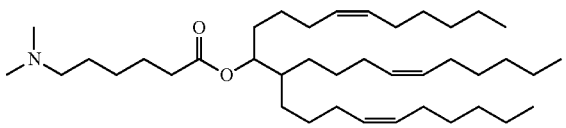

(6Z,16Z)-12-((Z)-dec-4-enyl)docosa-6,16-dien-11-yl 6-(dimethylamino)hexanoate (11)

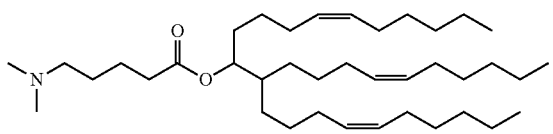

(6Z,16Z)-12-((Z)-dec-4-enyl)docosa-6,16-dien-11-yl 5-(dimethylamino)pentanoate (13)

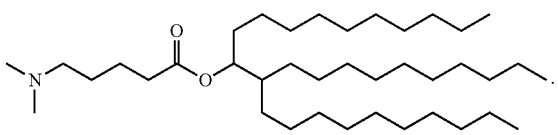

12-decyldocosan-11-yl 5-(dimethylamino)pentanoate (14)

Non-Cationic Lipids

The non-cationic lipids used in the lipid particles can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127060, the disclosure of which is herein incorporated by reference in its entirety for all purposes.

In some embodiments, the non-cationic lipid present in the lipid particles comprises or consists of a mixture of one or more phospholipids and cholesterol or a derivative thereof. In other embodiments, the non-cationic lipid present in the lipid particles comprises or consists of one or more phospholipids, e.g., a cholesterol-free lipid particle formulation. In yet other embodiments, the non-cationic lipid present in the lipid particles comprises or consists of cholesterol or a derivative thereof, e.g., a phospholipid-free lipid particle formulation.

Other examples of non-cationic lipids suitable for use include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 45 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In an certain embodiments, the phospholipid component in the mixture comprises from about 5 mol % to about 17 mol %, from about 7 mol % to about 17 mol %, from about 7 mol % to about 15 mol %, from about 8 mol % to about 15 mol %, or about 8 mol %, 9 mol %, 10 mol %, 11 mol %, 12 mol %, 13 mol %, 14 mol %, or 15 mol % (or any fraction thereof or range therein) of the total lipid present in the particle. As a non-limiting example, a lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

By way of further example, a lipid formulation useful has a lipid to therapeutic agent (e.g., nucleic acid) ratio of about 10:1 (e.g., a lipid:therapeutic agent ratio of from 9.5:1 to 11:1, or from 9.9:1 to 11:1, or from 10:1 to 10.9:1). In certain other embodiments, a lipid formulation useful has a lipid to therapeutic agent (e.g., nucleic acid) ratio of about 9:1 (e.g., a lipid:therapeutic agent ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1).

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle. As a non-limiting example, a lipid particle formulation may comprise cholesterol at about 37 mol % (or any fraction thereof) of the total lipid present in the particle. As another non-limiting example, a lipid particle formulation may comprise cholesterol at about 35 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol or derivative thereof) (or any fraction thereof or range therein) of the total lipid present in the particle.

Additional percentages and ranges of non-cationic lipids suitable for use in the lipid particles are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

It should be understood that the percentage of non-cationic lipid present in the lipid particles is a target amount, and that the actual amount of non-cationic lipid present in the formulation may vary, for example, by ±5 mol %, ±4 mol %, ±3 mol %, ±2 mol %, ±1 mol %, ±0.75 mol %, ±0.5 mol %, ±0.25 mol %, or 0.1 mol %.

Lipid Conjugates

In addition to cationic and non-cationic lipids, the lipid particles may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid conjugate. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use include, without limitation, mPEG2000-1,2-di-O-alkyl-sn3-carbomoylglyceride (PEG-C-DOMG). The synthesis of PEG-C-DOMG is described in PCT Publication No. WO 09/086558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-dioxaoctanyl]carbamoyl-ω-methyl-poly(ethylene glycol) (2KPEG-DMG). The synthesis of 2KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S—NHS, HO-PEG-NH$_2$, etc.). Other PEGs such as those described in U.S. Pat. Nos. 6,774,180 and 7,053,150 (e.g., mPEG (20 KDa) amine) are also useful for preparing the PEG-lipid conjugates. The disclosures of these patents are herein incorporated by reference in their entirety for all purposes. In addition, monomethoxypolyethyleneglycol-acetic acid (MePEG-CH$_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)-), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O-(O)POH-O-), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skill in the art. Phosphatidyl-ethanolamines containing saturated or unsaturated fatty acids with carbon chain lengths in the range of C$_{10}$ to C$_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and di stearoyl-phosphatidylethanolamine (DSPE).

The term "ATTA" or "polyamide" includes, without limitation, compounds described in U.S. Pat. Nos. 6,320,017 and 6,586,559, the disclosures of which are herein incorporated by reference in their entirety for all purposes. These compounds include a compound having the formula:

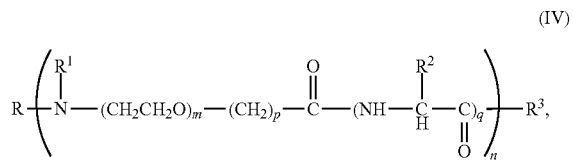

wherein R is a member selected from the group consisting of hydrogen, alkyl and acyl; R$^1$ is a member selected from the group consisting of hydrogen and alkyl; or optionally, R and R$^1$ and the nitrogen to which they are bound form an azido moiety; R$^2$ is a member of the group selected from hydrogen, optionally substituted alkyl, optionally substituted aryl and a side chain of an amino acid; R$^3$ is a member selected from the group consisting of hydrogen, halogen, hydroxy, alkoxy, mercapto, hydrazino, amino and NR$^4$R$^5$, wherein R$^4$ and R$^5$ are independently hydrogen or alkyl; n is 4 to 80; m is 2 to 6; p is 1 to 4; and q is 0 or 1. It will be apparent to those of skill in the art that other polyamides can be.

The term "diacylglycerol" or "DAG" includes a compound having 2 fatty acyl chains, R$^1$ and R$^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl (C$_{12}$), myristoyl (C$_{14}$), palmitoyl (C$_{16}$), stearoyl (C$_{18}$), and icosoyl (C$_{20}$). In preferred embodiments, R$^1$ and R$^2$ are the same, i.e., R$^1$ and R$^2$ are both myristoyl (i.e., dimyristoyl), R$^1$ and R$^2$ are both stearoyl (i.e., distearoyl), etc. Diacylglycerols have the following general formula:

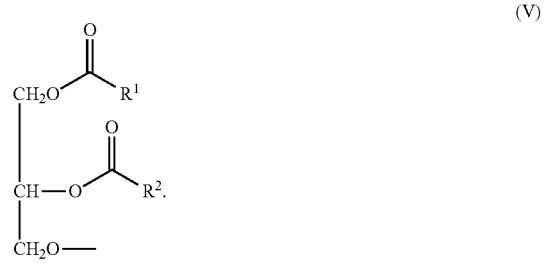

The term "dialkyloxypropyl" or "DAA" includes a compound having 2 alkyl chains, R$^1$ and R$^2$, both of which have independently between 2 and 30 carbons. The alkyl groups can be saturated or have varying degrees of unsaturation. Dialkyloxypropyls have the following general formula:

In a preferred embodiment, the PEG-lipid is a PEG-DAA conjugate having the following formula:

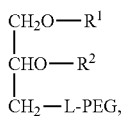

(VII)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VII above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

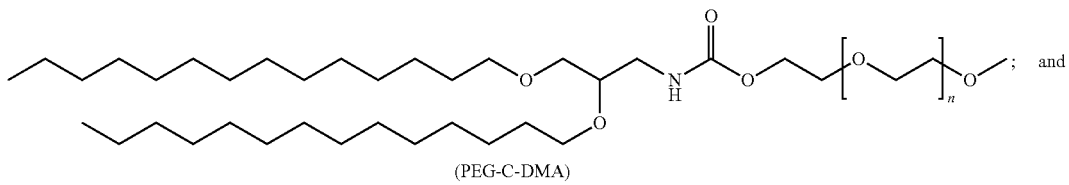

(66)

(PEG-C-DMA)

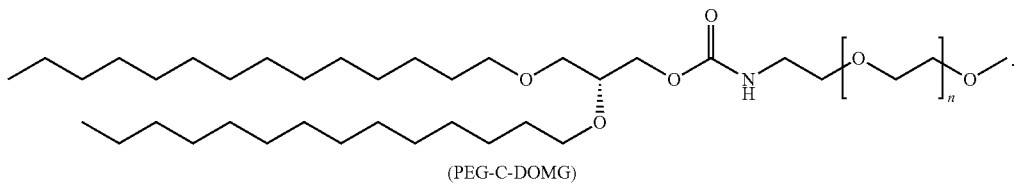

(67)

(PEG-C-DOMG)

In addition to the foregoing components, the lipid particles can further comprise cationic poly(ethylene glycol) (PEG) lipids or CPLs (see, e.g., Chen et al., *Bioconj. Chem.*, 11:433-437 (2000); U.S. Pat. No. 6,852,334; PCT Publication No. WO 00/62813, the disclosures of which are herein incorporated by reference in their entirety for all purposes).

Suitable CPLs include compounds of Formula VIII:

A-W-Y (VIII), wherein A, W, and Y are as described below.

With reference to Formula VIII, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N-N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0.1 mol % to about 3 mol %, from about 0.5 mol % to about 3 mol %, or about 0.6 mol %, 0.7 mol %, 0.8 mol %, 0.9 mol %, 1.0 mol %, 1.1 mol %, 1.2 mol %, 1.3 mol %, 1.4 mol %, 1.5 mol %, 1.6 mol %, 1.7 mol %, 1.8 mol %, 1.9 mol %, 2.0 mol %, 2.1 mol %, 2.2 mol %, 2.3 mol %, 2.4 mol %, 2.5 mol %, 2.6 mol %, 2.7 mol %, 2.8 mol %, 2.9 mol % or 3 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

It should be understood that the percentage of lipid conjugate present in the lipid particles is a target amount, and that the actual amount of lipid conjugate present in the formulation may vary, for example, by +5 mol %, +4 mol %, +3 mol %, +2 mol %, +1 mol %, +0.75 mol %, +0.5 mol %, +0.25 mol %, or ±0.1 mol %.

Additional percentages and ranges of lipid conjugates suitable for use in the lipid particles are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle size.

Description of Certain Therapeutic Agent-Lipid Particle Embodiments

A therapeutic agent-lipid particle typically may comprise one or more therapeutic agents, such as one or more nucleic acid molecules (e.g., a cocktail), a cationic lipid, and a non-cationic lipid. In certain instances, the therapeutic agent-lipid particles further comprise a conjugated lipid that inhibits aggregation of particles.

In some embodiments, the therapeutic agent (e.g., a nucleic acid molecule, such as a siRNA or mRNA) is fully encapsulated in the therapeutic agent-lipid particle. With respect to formulations comprising a cocktail of therapeutic agents, the different types of species present in the cocktail (e.g., siRNA compounds with different sequences) may be co-encapsulated in the same particle, or each type of species present in the cocktail may be encapsulated in a separate particle. The cocktail may be formulated in the particles described herein using a mixture of two, three or more individual agents (e.g., individuals nucleic acid molecules, each having a unique sequence) at identical, similar, or different concentrations or molar ratios. In one embodiment, a cocktail of nucleic acid molecules (corresponding to a plurality of nucleic acid molecules with different sequences) is formulated using identical, similar, or different concentrations or molar ratios of each species, and the different types of molecules are co-encapsulated in the same particle. In another embodiment, each type of nucleic acid molecule species present in the cocktail is encapsulated in different particles at identical, similar, or different nucleic acid molecule concentrations or molar ratios, and the particles thus formed (each containing a different nucleic acid molecule payload) are administered separately (e.g., at different times in accordance with a therapeutic regimen), or are combined and administered together as a single unit dose (e.g., with a pharmaceutically acceptable carrier). The particles described herein are serum-stable, are resistant to nuclease degradation, and are substantially non-toxic to mammals such as humans.

The cationic lipid in the therapeutic agent-lipid particles of the invention may comprise, e.g., one or more cationic lipids of Formula I-III described herein or any other cationic lipid species. In one embodiment, cationic lipid is a dialkyl lipid. In another embodiment, the cationic lipid is a trialkyl lipid. In one particular embodiment, the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA; Compound (15)), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), dilinoleylmethyl-3-dimethylaminopropionate (DLin-M-C2-DMA), (6Z,9Z,28Z,31Z)-heptatriaconta-6,9,28,31-tetraen-19-yl 4-(dimethylamino)butanoate (DLin-M-C3-DMA; Compound (7)), salts thereof, and mixtures thereof.

In another particular embodiment, the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA; Compound (15)), 3-((6Z,9Z,28Z,31Z)-heptatriaconta-6,9,28,31-tetraen-19-yloxy)-N,N-dimethylpropan-1-amine (DLin-MP-DMA; Compound (8)), (6Z,9Z,28Z,31Z)-heptatriaconta-6,9,28,31-tetraen-19-yl 4-(dimethylamino)butanoate) (Compound (7)), (6Z,16Z)-12-((Z)-dec-4-enyl)docosa-6,16-dien-11-yl 5-(dimethylamino)pentanoate (Compound (13)), a salt thereof, or a mixture thereof.

In certain embodiments, the cationic lipid comprises from about 48 mol % to about 62 mol % of the total lipid present in the particle.

The non-cationic lipid in the therapeutic agent-lipid particles of the present invention may comprise, e.g., one or more anionic lipids and/or neutral lipids. In some embodiments, the non-cationic lipid comprises one of the following neutral lipid components: (1) a mixture of a phospholipid and cholesterol or a derivative thereof; (2) cholesterol or a derivative thereof; or (3) a phospholipid. In certain preferred embodiments, the phospholipid comprises dipalmitoylphosphatidylcholine (DPPC), distearoylphosphatidylcholine (DSPC), or a mixture thereof. In a preferred embodiment, the non-cationic lipid is a mixture of DPPC and cholesterol. In a preferred embodiment, the non-cationic lipid is a mixture of DSPC and cholesterol.

In certain embodiments, the non-cationic lipid comprises a mixture of a phospholipid and cholesterol or a derivative thereof, wherein the phospholipid comprises from about 7 mol % to about 17 mol % of the total lipid present in the particle and the cholesterol or derivative thereof comprises from about 25 mol % to about 40 mol % of the total lipid present in the particle.

The lipid conjugate in the therapeutic agent-lipid particles of the invention inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-lipid conjugate is selected from the group consisting of a PEG-diacylglycerol (PEG-DAG) conjugate, a PEG-dialkyloxypropyl (PEG-DAA) conjugate, a PEG-phospholipid conjugate, a PEG-ceramide (PEG-Cer) conjugate, a PEG-dimyristyloxypropyl (PEG-DMA) conjugate and a mixture thereof. In certain embodiments, the PEG-lipid conjugate is a PEG-DAA conjugate. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, or mixtures thereof. In certain embodiments, wherein the PEG-DAA conjugate is a PEG-dimyristyloxypropyl ($C_{14}$) conjugate. In another embodiment, the PEG-DAA conjugate is a compound (66) (PEG-C-DMA) conjugate (e.g., PEG2000-C-DMA). In another embodiment, the lipid conjugate comprises a POZ-lipid conjugate such as a POZ-DAA conjugate.

In certain embodiments, the conjugated lipid that inhibits aggregation of particles comprises from about 0.5 mol % to about 3 mol % of the total lipid present in the particle.

In certain embodiments, the therapeutic agent-lipid particle has a total lipid:therapeutic agent mass ratio of from about 5:1 to about 15:1.

In certain embodiments, the therapeutic agent-lipid particle has a median diameter of from about 30 nm to about 150 nm.

In certain embodiments, the therapeutic agent-lipid particle has an electron dense core.

In some embodiments, the present invention provides therapeutic agent-lipid particles comprising: (a) at least one therapeutic agent; (b) one or more cationic lipids or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the therapeutic agent-lipid particle comprises: (a) at least one therapeutic agent; (b) a cationic lipid or a salt thereof comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. In one particular embodiment, the formulation is a four-component system comprising about 1.4 mol % PEG-lipid conjugate (e.g., PEG2000-C-DMA), about 57.1 mol % cationic lipid (e.g., DLin-K-C2-DMA) or a salt thereof, about 7.1 mol % DPPC (or DSPC), and about 34.3 mol % cholesterol (or derivative thereof).

In another aspect of this embodiment, the therapeutic agent-lipid particle comprises: (a) at least one therapeutic agent; (b) a cationic lipid or a salt thereof comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. In one particular embodiment, the formulation is a three-component system which is phospholipid-free and comprises about 1.5 mol % PEG-lipid conjugate (e.g., PEG2000-C-DMA), about 61.5 mol % cationic lipid (e.g., DLin-K-C2-DMA) or a salt thereof, and about 36.9 mol % cholesterol (or derivative thereof).

Additional formulations are described in PCT Publication No. WO 09/127060 and published US patent application publication number US 2011/0071208 A1, the disclosures of which are herein incorporated by reference in their entirety for all purposes.

In other embodiments, the present invention provides therapeutic agent-lipid particles comprising: (a) at least one therapeutic agent; (b) one or more cationic lipids or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the therapeutic agent-lipid particle comprises: (a) at least one therapeutic agent; (b) a cationic lipid or a salt thereof comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. In one particular embodiment, the formulation is a four-component system which comprises about 2 mol % PEG-lipid conjugate (e.g., PEG2000-C-DMA), about 40 mol % cationic lipid (e.g., DLin-K-C2-DMA) or a salt thereof, about 10 mol % DPPC (or DSPC), and about 48 mol % cholesterol (or derivative thereof).

In further embodiments, the present invention provides therapeutic agent-lipid particles comprising: (a) at least one therapeutic agent; (b) one or more cationic lipids or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In one aspect of this embodiment, the therapeutic agent-lipid particle comprises: (a) at least one therapeutic agent; (b) a cationic lipid or a salt thereof comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle. In certain instances, the non-cationic lipid mixture in the formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the formulation is a four-component system which comprises about 7 mol % PEG-lipid conjugate (e.g., PEG750-C-DMA), about 54 mol % cationic lipid (e.g., DLin-K-C2-DMA) or a salt thereof, about 7 mol % DPPC (or DSPC), and about 32 mol % cholesterol (or derivative thereof).

In another aspect of this embodiment, the therapeutic agent-lipid particle comprises: (a) at least one therapeutic agent; (b) a cationic lipid or a salt thereof comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. In one particular embodiment, the formulation is a three-component system which is phospholipid-free and comprises about 7 mol % PEG-lipid conjugate (e.g., PEG750-C-DMA), about 58 mol % cationic lipid (e.g., DLin-K-C2-DMA) or a salt thereof, and about 35 mol % cholesterol (or derivative thereof).

Additional embodiments of useful formulations are described in published US patent application publication number US 2011/0076335 A1, the disclosure of which is herein incorporated by reference in its entirety for all purposes.

In certain embodiments of the invention, the therapeutic agent-lipid particle comprises: (a) at least one therapeutic agent; (b) a cationic lipid or a salt thereof comprising from about 48 mol % to about 62 mol % of the total lipid present in the particle; (c) a mixture of a phospholipid and cholesterol or a derivative thereof, wherein the phospholipid comprises about 7 mol % to about 17 mol % of the total lipid present in the particle, and wherein the cholesterol or derivative thereof comprises about 25 mol % to about 40 mol % of the total lipid present in the particle; and (d) a PEG-lipid conjugate comprising from about 0.5 mol % to about 3.0 mol % of the total lipid present in the particle. Exemplary lipid formulations A-Z of this aspect of the invention are included below.

Exemplary lipid formulation A includes the following components (wherein the percentage values of the components are mole percent): PEG-lipid (1.2%), cationic lipid (53.2%), phospholipid (9.3%), cholesterol (36.4%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.2%), the cationic lipid is 1,2-dilinoleyloxy-N,N-dimethylaminopropane (DLinDMA) (53.2%), the phospholipid is DPPC (9.3%), and cholesterol is present at 36.4%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation A, which comprises at least one therapeutic agent described herein (e.g., a nucleic acid molecule).

Exemplary lipid formulation B which includes the following components (wherein the percentage values of the components are mole percent): PEG-lipid (0.8%), cationic lipid (59.7%), phospholipid (14.2%), cholesterol (25.3%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (0.8%), the cationic lipid is 1,2-dilinoleyloxy-N,N-dimethylaminopropane (DLinDMA) (59.7%), the phospholipid is DSPC (14.2%), and cholesterol is present at 25.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation B, which comprises at least one therapeutic agent described herein (e.g., a nucleic acid molecule).

Exemplary lipid formulation C includes the following components (wherein the percentage values of the components are mole percent): PEG-lipid (1.9%), cationic lipid (52.5%), phospholipid (14.8%), cholesterol (30.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (1.9%), the cationic lipid is 1,2-di-γ-linolenyloxy-N,N-dimethylaminopropane (γ-DLenDMA; Compound (15)) (52.5%), the phospholipid is DSPC (14.8%), and cholesterol is present at 30.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation C, which comprises at least one therapeutic agent described herein (e.g., a nucleic acid molecule).

Exemplary lipid formulation D includes the following components (wherein the percentage values of the components are mole percent): PEG-lipid (0.7%), cationic lipid (60.3%), phospholipid (8.4%), cholesterol (30.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (0.7%), the cationic lipid is 3-((6Z,9Z,28Z,31Z)-heptatriaconta-6,9,28,31-tetraen-19-yloxy)-N,N-dimethylpropan-1-amine (DLin-MP-DMA; Compound (8) (60.3%), the phospholipid is DSPC (8.4%), and cholesterol is present at 30.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation D, which comprises at least one therapeutic agent described herein (e.g., a nucleic acid molecule).

Exemplary lipid formulation E includes the following components (wherein the percentage values of the components are mole percent): PEG-lipid (1.8%), cationic lipid (52.1%), phospholipid (7.5%), cholesterol (38.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.8%), the cationic lipid is (6Z,9Z,28Z,31Z)-heptatriaconta-6,9,28,31-tetraen-19-yl 4-(dimethylamino)butanoate) (Compound (7)) (52.1%), the phospholipid is DPPC (7.5%), and cholesterol is present at 38.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation E, which comprises at least one therapeutic agent described herein (e.g., a nucleic acid molecule).

Exemplary formulation F includes the following components (wherein the percentage values of the components are mole percent): PEG-lipid (0.9%), cationic lipid (57.1%), phospholipid (8.1%), cholesterol (33.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (0.9%), the cationic lipid is 1,2-dilinolenyloxy-N,N-dimethylaminopropane (DLenDMA), 1,2-di-γ-linolenyloxy-N,N-dimethylaminopropane (γ-DLenDMA; Compound (15)) (57.1%), the phospholipid is DSPC (8.1%), and cholesterol is present at 33.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation F, which comprises at least one therapeutic agent described herein (e.g., a nucleic acid molecule).

Exemplary lipid formulation G includes the following components (wherein the percentage values of the components are mole percent): PEG-lipid (1.7%), cationic lipid (61.6%), phospholipid (11.2%), cholesterol (25.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (1.7%), the cationic lipid is 1,2-dilinolenyloxy-N,N-dimethylaminopropane (DLenDMA), 1,2-di-γ-linolenyloxy-N,N-dimethylaminopropane (γ-DLenDMA; Compound (15)) (61.6%), the phospholipid is DPPC (11.2%), and cholesterol is present at 25.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation G, which comprises at least one therapeutic agent described herein (e.g., a nucleic acid molecule).

Exemplary lipid formulation H includes the following components (wherein the percentage values of the components are mole percent): PEG-lipid (1.1%), cationic lipid (55.0%), phospholipid (11.0%), cholesterol (33.0%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.1%), the cationic lipid is (6Z,16Z)-12-((Z)-dec-4-enyl)docosa-6,16-dien-11-yl 5-(dimethylamino)pentanoate (Compound (13)) (55.0%), the phospholipid is DSPC (11.0%), and cholesterol is present at 33.0%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation H, which comprises at least one therapeutic agent described herein (e.g., a nucleic acid molecule).

Exemplary lipid formulation I includes the following components (wherein the percentage values of the components are mole percent): PEG-lipid (2.6%), cationic lipid (53.1%), phospholipid (9.4%), cholesterol (35.0%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.6%), the cationic lipid is (6Z,16Z)-12-((Z)-dec-4-enyl)docosa-6,16-dien-11-yl 5-(dimethylamino)pentanoate (Compound (13)) (53.1%), the phospholipid is DSPC (9.4%), and cholesterol is present at 35.0%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation I, which comprises at least one therapeutic agent described herein (e.g., a nucleic acid molecule).

Exemplary lipid formulation J includes the following components (wherein the percentage values of the components are mole percent): PEG-lipid (0.6%), cationic lipid (59.4%), phospholipid (10.2%), cholesterol (29.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (0.6%), the cationic lipid is 1,2-dilinoleyloxy-N,N-dimethylaminopropane (DLinDMA) (59.4%), the phospholipid is DPPC (10.2%), and cholesterol is present at 29.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation J, which comprises at least one therapeutic agent described herein (e.g., a nucleic acid molecule).

Exemplary lipid formulation K includes the following components (wherein the percentage values of the components are mole percent): PEG-lipid (0.5%), cationic lipid (56.7%), phospholipid (13.1%), cholesterol (29.7%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (0.5%), the cationic lipid is (6Z,9Z,28Z,31Z)-heptatriaconta-6,9,28,31-tetraen-19-yl 4-(dimethylamino)butanoate) (Compound (7)) (56.7%), the phospholipid is DSPC (13.1%), and cholesterol is present at 29.7%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation K, which comprises at least one therapeutic agent described herein (e.g., a nucleic acid molecule).

Exemplary lipid formulation L includes the following components (wherein the percentage values of the components are mole percent): PEG-lipid (2.2%), cationic lipid (52.0%), phospholipid (9.7%), cholesterol (36.2%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (2.2%), the cationic lipid is 1,2-di-γ-linolenyloxy-N,N-dimethylaminopropane (γ-DLenDMA; Compound (15)) (52.0%), the phospholipid is DSPC (9.7%), and cholesterol is present at 36.2%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or 0.1 mol %). Thus, certain embodiments of the invention provide a therapeutic agent-lipid particle based on formulation L, which comprises at least one therapeutic agent described herein (e.g., a nucleic acid molecule).

Exemplary lipid formulation M includes the following components (wherein the percentage values of the components are mole percent): PEG-lipid (2.7%), cationic lipid (58.4%), phospholipid (13.1%), cholesterol (25.7%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.7%), the cationic lipid is 1,2-dilinoleyloxy-N,N-dimethylaminopropane (DLinDMA) (58.4%), the phospholipid is DPPC (13.1%), and cholesterol is present at 25.7%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation M, which comprises at least one therapeutic agent described herein (e.g., a nucleic acid molecule).

Exemplary lipid formulation N includes the following components (wherein the percentage values of the components are mole percent): PEG-lipid (3.0%), cationic lipid (53.3%), phospholipid (12.1%), cholesterol (31.5%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (3.0%), the cationic lipid is 1,2-dilinoleyloxy-N,N-dimethylaminopropane (DLinDMA) (53.3%), the phospholipid is DPPC (12.1%), and cholesterol is present at 31.5%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation N, which comprises at least one therapeutic agent described herein (e.g., a nucleic acid molecule).

Exemplary lipid formulation O includes the following components (wherein the percentage values of the components are mole percent): PEG-lipid (1.5%), cationic lipid (56.2%), phospholipid (7.8%), cholesterol (34.7%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.5%), the cationic lipid is 1,2-dilinoleyloxy-N,N-dimethylaminopropane (DLinDMA) (56.2%), the phospholipid is DPPC (7.8%), and cholesterol is present at 34.7%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation O, which comprises at least one therapeutic agent described herein (e.g., a nucleic acid molecule).

Exemplary lipid formulation P includes the following components (wherein the percentage values of the components are mole percent): PEG-lipid (2.1%), cationic lipid (48.6%), phospholipid (15.5%), cholesterol (33.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DOMG (compound (67)) (2.1%), the cationic lipid is 3-((6Z,9Z,28Z,31Z)-heptatriaconta-6,9,28, 31-tetraen-19-yloxy)-N,N-dimethylpropan-1-amine (DLin-MP-DMA; Compound (8)) (48.6%), the phospholipid is DSPC (15.5%), and cholesterol is present at 33.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation P, which comprises at least one therapeutic agent described herein (e.g., a nucleic acid molecule).

Exemplary lipid formulation Q includes the following components (wherein the percentage values of the components are mole percent): PEG-lipid (2.5%), cationic lipid (57.9%), phospholipid (9.2%), cholesterol (30.3%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.5%), the cationic lipid is (6Z,16Z)-12-((Z)-dec-4-enyl)docosa-6,16-dien-11-yl 5-(dimethylamino)pentanoate (Compound (13)) (57.9%), the phospholipid is DSPC (9.2%), and cholesterol is present at 30.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or 0.1 mol %). Thus, certain embodiments of the invention provide a therapeutic agent-lipid particle based on formulation Q, which comprises at least one therapeutic agent described herein (e.g., a nucleic acid molecule).

Exemplary lipid formulation R includes the following components (wherein the percentage values of the components are mole percent): PEG-lipid (1.6%), cationic lipid (54.6%), phospholipid (10.9%), cholesterol (32.8%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (1.6%), the cationic lipid is 3-((6Z,9Z,28Z,31Z)-heptatriaconta-6,9,28, 31-tetraen-19-yloxy)-N,N-dimethylpropan-1-amine (Compound (8)) (54.6%), the phospholipid is DSPC (10.9%), and cholesterol is present at 32.8%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation R, which comprises at least one therapeutic agent described herein (e.g., a nucleic acid molecule).

Exemplary lipid formulation S includes the following components (wherein the percentage values of the components are mole percent): PEG-lipid (2.9%), cationic lipid (49.6%), phospholipid (16.3%), cholesterol (31.3%), wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). For example, in one representative embodiment, the PEG-lipid is PEG-C-DMA (compound (66)) (2.9%), the cationic lipid is (6Z,16Z)-12-((Z)-dec-4-enyl)docosa-6,16-dien-11-yl 5-(dimethylamino)pentanoate (Compound (13)) (49.6%), the phospholipid is DPPC (16.3%), and cholesterol is present at 31.3%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation S, which comprises at least one therapeutic agent described herein (e.g., a nucleic acid molecule).

Exemplary lipid formulation T includes the following components (wherein the percentage values of the components are mole percent): PEG-lipid (0.7%), cationic lipid (50.5%), phospholipid (8.9%), cholesterol (40.0%), wherein the actual amounts of the lipids present may vary by, e.g., ±5% (or e.g., ±4 mol %, ±3 mol %, +2 mol %, +1 mol %, +0.75 mol %, +0.5 mol %, +0.25 mol %, or +0.1 mol %). For example, in one representative embodiment, the PEG-lipid is PEG-C-DOMG (compound (67)) (0.7%), the cationic lipid is 1,2-dilinoleyloxy-N,N-dimethylaminopropane (DLinDMA) (50.5%), the phospholipid is DPPC (8.9%), and cholesterol is present at 40.0%, wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). Thus, certain embodiments of the invention provide a therapeutic agent-lipid particle based on formulation T, which comprises at least one therapeutic agent described herein (e.g., a nucleic acid molecule).

Exemplary lipid formulation U includes the following components (wherein the percentage values of the components are mole percent): PEG-lipid (1.0%), cationic lipid (51.4%), phospholipid (15.0%), cholesterol (32.6%), wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). For example, in one representative embodiment, the PEG-lipid is PEG-C-DOMG (compound (67)) (1.0%), the cationic lipid is 1,2-dilinoleyloxy-N,N-dimethylaminopropane (DLinDMA) (51.4%), the phospholipid is DSPC (15.0%), and cholesterol is present at 32.6%, wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). Thus, certain embodiments of the invention provide a therapeutic agent-lipid particle based on formulation U, which comprises at least one therapeutic agent described herein (e.g., a nucleic acid molecule).

Exemplary lipid formulation V includes the following components (wherein the percentage values of the components are mole percent): PEG-lipid (1.3%), cationic lipid (60.0%), phospholipid (7.2%), cholesterol (31.5%), wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). For example, in one representative embodiment, the PEG-lipid is PEG-C-DOMG (compound (67)) (1.3%), the cationic lipid is 1,2-dilinolenyloxy-N,N-dimethylaminopropane (DLenDMA) (60.0%), the phospholipid is DSPC (7.2%), and cholesterol is present at 31.5%, wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). Thus, certain embodiments of the invention provide a therapeutic agent-lipid particle based on formulation V, which comprises at least one therapeutic agent described herein (e.g., a nucleic acid molecule).

Exemplary lipid formulation W includes the following components (wherein the percentage values of the components are mole percent): PEG-lipid (1.8%), cationic lipid (51.6%), phospholipid (8.4%), cholesterol (38.3%), wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). For example, in one representative embodiment, the PEG-lipid is PEG-C-DMA (compound (66)) (1.8%), the cationic lipid is 1,2-dilinoleyloxy-N,N-dimethylaminopropane (DLinDMA) (51.6%), the phospholipid is DSPC (8.4%), and cholesterol is present at 38.3%, wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). Thus, certain embodiments of the invention provide a therapeutic agent-lipid particle based on formulation W, which comprises at least one therapeutic agent described herein (e.g., a nucleic acid molecule).

Exemplary lipid formulation X includes the following components (wherein the percentage values of the components are mole percent): PEG-lipid (2.4%), cationic lipid (48.5%), phospholipid (10.0%), cholesterol (39.2%), wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). For example, in one representative embodiment, the PEG-lipid is PEG-C-DMA (compound (66)) (2.4%), the cationic lipid is 1,2-di-γ-linolenyloxy-N,N-dimethylaminopropane (γ-DLenDMA; Compound (15)) (48.5%), the phospholipid is DPPC (10.0%), and cholesterol is present at 39.2%, wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). Thus, certain embodiments of the invention provide a therapeutic agent-lipid particle based on formulation X, which comprises at least one therapeutic agent described herein (e.g., a nucleic acid molecule).

Exemplary lipid formulation Y includes the following components (wherein the percentage values of the components are mole percent): PEG-lipid (2.6%), cationic lipid (61.2%), phospholipid (7.1%), cholesterol (29.2%), wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). For example, in one representative embodiment, the PEG-lipid is PEG-C-DMA (compound (66)) (2.6%), the cationic lipid is (6Z,16Z)-12-((Z)-dec-4-enyl)docosa-6,16-dien-11-yl 5-(dimethylamino)pentanoate (Compound (13)) (61.2%), the phospholipid is DSPC (7.1%), and cholesterol is present at 29.2%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or ±0.1 mol %). Thus, certain embodiments of the invention provide a therapeutic agent-lipid particle based on formulation Y, which comprises at least one therapeutic agent described herein (e.g., a nucleic acid molecule).

Exemplary lipid formulation Z includes the following components (wherein the percentage values of the components are mole percent): PEG-lipid (2.2%), cationic lipid (49.7%), phospholipid (12.1%), cholesterol (36.0%), wherein the actual amounts of the lipids present may vary by, e.g., +5% (or e.g., +4 mol %, +3 mol %, +2 mol %, +1 mol %, +0.75 mol %, +0.5 mol %, +0.25 mol %, or +0.1 mol %). For example, in one representative embodiment, the PEG-lipid is PEG-C-DOMG (compound (67)) (2.2%), the cationic lipid is (6Z,9Z,28Z,31Z)-heptatriaconta-6,9,28,31-tetraen-19-yl 4-(dimethylamino)butanoate) (Compound (7)) (49.7%), the phospholipid is DPPC (12.1%), and cholesterol is present at 36.0%, wherein the actual amounts of the lipids present may vary by, e.g., ±5% (or e.g., ±4 mol %, ±3 mol %, ±2 mol %, ±1 mol %, ±0.75 mol %, ±0.5 mol %, ±0.25 mol %, or 0.1 mol %). Thus, certain embodiments of the invention provide a therapeutic agent-lipid particle based on formulation Z, which comprises at least one therapeutic agent described herein (e.g., a nucleic acid molecule).

Accordingly, certain embodiments of the invention provide a therapeutic agent-lipid particle described herein, wherein the lipids are formulated as described in any one of formulations A, B, C, D, E, F, G, H, I, J, K, L, M, N, O, P, Q, R, S, T, U, V, W, X, Y or Z.

Preparation of Lipid Particles

The therapeutic agent-lipid particles, in which a therapeutic agent (e.g., a nucleic acid, such as a siRNA or mRNA) is entrapped within the lipid portion of the particle and is protected from degradation, can be formed by any method known in the art including, but not limited to, a continuous mixing method, a direct dilution process, and an in-line dilution process.

In particular embodiments, the cationic lipids may comprise lipids of Formula I-III or salts thereof, alone or in combination with other cationic lipids. In other embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphati dylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-di stearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphati dylethanolamine (SOPE)), 16:0-18:1 PE (1-palmitoyl-2-oleoylphosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the therapeutic agent-lipid particles produced via a continuous mixing method, e.g., a process that includes providing an aqueous solution comprising a therapeutic agent in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the therapeutic agent within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a therapeutic agent with the organic lipid solution, the organic lipid solution undergoes a continuous stepwise dilution in the presence of the buffer solution (i.e., aqueous solution) to produce a therapeutic agent-lipid particle.

The therapeutic agent-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the therapeutic agent-lipid particles produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the therapeutic agent-lipid particles produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The therapeutic agent-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

The lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the therapeutic agents present in the particles (e.g., nucleic acid molecules) are precondensed as described in, e.g., U.S. patent application Ser. No. 09/744, 103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the therapeutic agent (e.g., nucleic acid, such as siRNA or mRNA) to lipid ratios (mass/mass ratios) in a formed therapeutic agent-lipid particle will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 µg therapeutic agent per 10 mg total lipid or a therapeutic agent to lipid mass ratio of about 0.01 to about 0.08 and, more preferably, about 0.04, which corresponds to 1.25 mg of total lipid per 50 µg of therapeutic agent. In other preferred embodiments, the particle has a therapeutic agent:lipid mass ratio of about 0.08.

In other embodiments, the lipid to therapeutic agent (e.g., nucleic acid, such as siRNA or mRNA) ratios (mass/mass ratios) in a formed therapeutic agent-lipid particle will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making lipid particle-CPLs (CPL-containing lipid particles) are discussed herein. Two general techniques include the "post-insertion" technique, that is, insertion of a CPL into, for example, a pre-formed lipid particle, and the "standard" technique, wherein the CPL is included in the lipid mixture during, for example, the lipid particle formation steps. The post-insertion technique results in lipid particles having CPLs mainly in the external face of the lipid particle bilayer membrane, whereas standard techniques provide lipid particles having CPLs on both internal and external faces. The method is especially useful for vesicles made from phospholipids (which can contain cholesterol) and also for vesicles containing PEG-lipids (such as PEG-DAAs and PEG-DAGs). Methods of making lipid particle-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

Additional Carrier Systems

Non-limiting examples of additional lipid-based carrier systems suitable for use include lipoplexes (see, e.g., U.S. Patent Publication No. 20030203865; and Zhang et al., J. Control Release, 100:165-180 (2004)), pH-sensitive lipoplexes (see, e.g., U.S. Patent Publication No. 20020192275), reversibly masked lipoplexes (see, e.g., U.S. Patent Publication Nos. 20030180950), cationic lipid-based compositions (see, e.g., U.S. Pat. No. 6,756,054; and U.S. Patent Publication No. 20050234232), cationic liposomes (see, e.g., U.S. Patent Publication Nos. 20030229040, 20020160038, and 20020012998; U.S. Pat. No. 5,908,635; and PCT Publication No. WO 01/72283), anionic liposomes (see, e.g., U.S. Patent Publication No. 20030026831), pH-sensitive liposomes (see, e.g., U.S. Patent Publication No. 20020192274; and AU 2003210303), antibody-coated liposomes (see, e.g., U.S. Patent Publication No. 20030108597; and PCT Publication No. WO 00/50008), cell-type specific liposomes (see, e.g., U.S. Patent Publication No. 20030198664), liposomes containing nucleic acid and peptides (see, e.g., U.S. Pat. No. 6,207,456), liposomes containing lipids derivatized with releasable hydrophilic polymers (see, e.g., U.S. Patent Publication No. 20030031704), lipid-entrapped nucleic acid (see, e.g., PCT Publication Nos. WO 03/057190 and WO 03/059322), lipid-encapsulated nucleic acid (see, e.g., U.S. Patent Publication No. 20030129221; and U.S. Pat. No. 5,756,122), other liposomal compositions (see, e.g., U.S. Patent Publication Nos. 20030035829 and 20030072794; and U.S. Pat. No. 6,200, 599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 20050037086).

Examples of polymer-based carrier systems suitable for use include, but are not limited to, cationic polymer-nucleic acid complexes (i.e., polyplexes). To form a polyplex, a nucleic acid (e.g., a siRNA molecule or mRNA molecule) is typically complexed with a cationic polymer having a linear, branched, star, or dendritic polymeric structure that condenses the nucleic acid into positively charged particles capable of interacting with anionic proteoglycans at the cell surface and entering cells by endocytosis. In some embodiments, the polyplex comprises nucleic acid complexed with a cationic polymer such as polyethylenimine (PEI) (see, e.g., U.S. Pat. No. 6,013,240; commercially available from Qbiogene, Inc. (Carlsbad, Calif.) as In vivo jetPEF™, a linear form of PEI), polypropylenimine (PPI), polyvinylpyrrolidone (PVP), poly-L-lysine (PLL), diethylaminoethyl (DEAE)-dextran, poly(β-amino ester) (PAE) polymers (see, e.g., Lynn et al., J. Am. Chem. Soc., 123:8155-8156 (2001)), chitosan, polyamidoamine (PAMAM) dendrimers (see, e.g., Kukowska-Latallo et al., Proc. Natl. Acad. Sci. USA, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., J. Control Release, 100:165-180 (2004); and Tiera et al., Curr. Gene Ther., 6:59-71 (2006)), and a mixture thereof. In other embodiments, the polyplex comprises cationic polymer-nucleic acid complexes as described in U.S. Patent Publication Nos. 20060211643, 20050222064, 20030125281, and 20030185890, and PCT Publication No. WO 03/066069; biodegradable poly(β-amino ester) polymer-nucleic acid complexes as described in U.S. Patent Publication No. 20040071654; microparticles containing polymeric matrices as described in U.S. Patent Publication No. 20040142475; other microparticle compositions as described in U.S. Patent Publication No. 20030157030; condensed nucleic acid complexes as described in U.S. Patent Publication No. 20050123600; and nanocapsule and microcapsule compositions as described in AU 2002358514 and PCT Publication No. WO 02/096551.

In certain instances, a nucleic acid may be complexed with cyclodextrin or a polymer thereof. Non-limiting examples of cyclodextrin-based carrier systems include the cyclodextrin-modified polymer-nucleic acid complexes described in U.S. Patent Publication No. 20040087024; the linear cyclodextrin copolymer-nucleic acid complexes described in U.S. Pat. Nos. 6,509,323, 6,884,789, and 7,091,192; and the cyclodextrin polymer-complexing agent-nucleic acid complexes described in U.S. Pat. No. 7,018,609. In certain other instances, a nucleic acid may be complexed with a peptide or polypeptide. An example of a protein-based carrier system includes, but is not limited to, the cationic oligopeptide-nucleic acid complex described in PCT Publication No. WO95/21931.

Administration of Lipid Particles

The lipid particles (e.g., a therapeutic agent-lipid particle, such as a nucleic-acid lipid particle) can be adsorbed to almost any cell type with which they are mixed or contacted. Once adsorbed, the particles can either be endocytosed by a portion of the cells, exchange lipids with cell membranes, or fuse with the cells. Transfer or incorporation of the therapeutic agent portion of the particle can take place via any one of these pathways. In particular, when fusion takes place, the particle membrane is integrated into the cell membrane and the contents of the particle combine with the intracellular fluid.

The lipid particles (e.g., therapeutic agent-lipid particles) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In Vivo Administration

Systemic delivery for in vivo therapy, e.g., delivery of a therapeutic agent described herein, such as a nucleic acid, to a distal target cell via body systems such as the circulation, has been achieved using therapeutic agent-lipid particles such as those described in PCT Publication Nos. WO 05/007196, WO 05/121348, WO 05/120152, and WO 04/002453, the disclosures of which are herein incorporated by reference in their entirety for all purposes.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., Methods Enzymol., 101:512 (1983); Mannino et al., Biotechniques, 6:682 (1988); Nicolau et al., Crit. Rev. Ther. Drug Carrier Syst., 6:239 (1989); and Behr, Acc. Chem. Res., 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

In embodiments where the lipid particles are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In some embodiments, the presence of a therapeutic agent, such as a nucleic acid molecule, is detectable in cells at about 8, 12, 24, 36, 48, 60, 72 or 96 hours after administration. In some embodiments, the effect of a therapeutic agent, such as a nucleic acid molecule, is detectable in cells at about 8, 12, 24, 36, 48, 60, 72 or 96 hours after administration. In other embodiments, downregulation of expression of a target sequence, such as a viral or host sequence, by a siRNA molecule is detectable at about 8, 12, 24, 36, 48, 60, 72 or 96 hours after administration. In yet other embodiments, downregulation of expression of a target sequence, such as a viral or host sequence, by a siRNA molecule occurs preferentially in infected cells and/or cells capable of being infected. In further embodiments, the presence or effect of a therapeutic agent in cells at a site proximal or distal to the site of administration is detectable at about 12, 24, 48, 72, or 96 hours, or at about 6, 8, 10, 12, 14, 16, 18, 19, 20, 22, 24, 26, or 28 days after administration. In additional embodiments, the lipid particles are administered parenterally or intraperitoneally.

The compositions, either alone or in combination with other suitable components, can be made into aerosol formulations (i.e., they can be "nebulized") to be administered via inhalation (e.g., intranasally or intratracheally) (see, Brigham et al., *Am. J. Sci.*, 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidylglycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Generally, when administered intravenously, the lipid particle formulations are formulated with a suitable pharmaceutical carrier. Suitable formulations are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic agent (e.g., a nucleic acid molecule) suspended in diluents such as water, saline, or PEG 400; (b) capsules, sachets, or tablets, each containing a predetermined amount of a therapeutic agent, as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic agent in a flavor, e.g., sucrose, as well as pastilles comprising the therapeutic agent in an inert base, such as gelatin and glycerin or sucrose and acacia emulsions, gels, and the like containing, in addition to the therapeutic agent, carriers known in the art.

In another example of their use, lipid particles can be incorporated into a broad range of topical dosage forms. For instance, a suspension containing therapeutic agent-lipid particles can be formulated and administered as gels, oils, emulsions, topical creams, pastes, ointments, lotions, foams, mousses, and the like.

The amount of particles administered will depend upon the ratio of therapeutic agent to lipid, the particular therapeutic agent used, the disease or condition being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

In certain embodiments, the therapeutic agent is administered via a therapeutic agent lipid particle.

In certain embodiments, with respect to methods that include the use of a cocktail of therapeutic agents (e.g., a cocktail of nucleic acid molecules) encapsulated within lipid particles, the different therapeutic agents are co-encapsulated in the same lipid particle.

In certain embodiments, the with respect to methods that include the use of a cocktail of therapeutic agents (e.g., a cocktail of nucleic acid molecules) encapsulated within lipid particles, each type of therapeutic agent species present in the cocktail is encapsulated in its own particle.

In certain embodiments, the with respect to methods that include the use of a cocktail of therapeutic agents (e.g., a cocktail of nucleic acid molecules) encapsulated within lipid particles, some therapeutic agent species are co-encapsulated in the same particle while other therapeutic agent species are encapsulated in different particles.

Formulation and Administration of NSAID and/or Additional Therapeutic Agent(s) As discussed herein, certain embodiments of the invention provide for the administration of a NSAID prior to at least one lipid formulated therapeutic agent being administered. In certain embodiments of the invention, a NSAID is administered via injection and at least one lipid formulated therapeutic agent is intravenously administered (i.e., administered sequentially in order). Additionally, in certain embodiments, one or more additional therapeutic agents may also be administered (e.g., simultaneously or sequentially with the NSAID and/or the at least one lipid formulated therapeutic agent). Thus, these agents may be administered to a mammal as indicated below.

It will be understood that agents can be formulated together in a single preparation or that they can be formulated separately and, thus, administered separately, either simultaneously or sequentially. In one embodiment, when the agents are administered sequentially (e.g. at different times), the agents may be administered so that their biological effects overlap (i.e. each agent is producing a biological effect at a single given time).

The agents can be formulated for and administered using any acceptable route of administration depending on the agent selected. For example, suitable routes include, but are not limited to, oral, sublingual, buccal, topical, transdermal, parenteral, subcutaneous, intraperitoneal, intrapulmonary, and intranasal, and, if desired for local treatment, intralesional administration. In one embodiment, the small molecule agents identified herein can be administered orally or by injection (e.g., into a blood vessel, such as a vein). In another embodiment, the nucleic acid molecules can be administered by injection (e.g., into a blood vessel, such as a vein), or subcutaneously.

Typically, the NSAID is administered via injection and the at least one lipid formulated therapeutic agent is administered intravenously. In certain embodiments, the NSAID is administered parenterally. In certain embodiments, the NSAID is administered intravenously.

In certain embodiments, the NSAID is administered intramuscularly. In certain embodiments, the NSAID is administered subcutaneously.

The agents can be individually formulated by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may typically range anywhere from about 3 to about 8. The agents ordinarily will be stored as a solid composition, although lyophilized formulations or aqueous solutions are acceptable.

Compositions comprising the agents can be formulated, dosed, and administered in a fashion consistent with good medical practice. Factors for consideration in this context include the particular disease or condition being treated, the particular mammal being treated, the clinical condition of the individual patient, the cause of the disorder, the site of administration, the method of administration, the scheduling of administration, and other factors known to medical practitioners.

The agents may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, *Williams & Wilkins,* 2004; Gennaro, Alfonso R., et al. *Remington: The Science and Practice of Pharmacy*. Philadelphia: Lippincott, *Williams & Wilkins,* 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug or aid in the manufacturing of the pharmaceutical product (i.e., medicament).

The agents are typically dosed at least at a level to reach the desired biological effect. Thus, an effective dosing regimen will dose at least a minimum amount that reaches the desired biological effect, or biologically effective dose, however, the dose should not be so high as to outweigh the benefit of the biological effect with unacceptable side effects. Therefore, an effective dosing regimen will dose no more than the maximum tolerated dose ("MTD"). The maximum tolerated dose is defined as the highest dose that produces an acceptable incidence of dose-limiting toxicities ("DLT"). Doses that cause an unacceptable rate of DLT are considered non-tolerated. Typically, the MTD for a particular schedule is established in phase 1 clinical trials. These are usually conducted in patients by starting at a safe starting dose of $\frac{1}{10}$ the severe toxic dose ("STD10") in rodents (on a mg/m² basis) and accruing patients in cohorts of three, escalating the dose according to a modified Fibonacci sequence in which ever higher escalation steps have ever decreasing relative increments (e.g., dose increases of 100%, 65%, 50%, 40%, and 30% to 35% thereafter). The dose escalation is continued in cohorts of three patients until a non-tolerated dose is reached. The next lower dose level that produces an acceptable rate of DLT is considered to be the MTD.

The amount of the agents administered will depend upon the particular agent used, the disease or condition being treated, the age, weight, and condition of the patient, and the judgment of the clinician, but will generally be between about 0.2 to 2.0 grams per day. For example, in certain embodiments, the NSAID is administered in an approved dosage for injection. In certain embodiments, the NSAID is administered in a dose of about 1 mg to about 1000 mg. In certain embodiments, a dose of the NSAID is administered one or more times per day. For example, in certain embodiments, the NSAID is ketorolac formulated for injection, wherein a single dose ranging between about 15 mg to about 60 mg is administered (e.g., about 30 mg to about 60 mg) or wherein a dose of about 15 mg to about 30 mg is administered multiple times in a day (e.g., a dose is administered every 6 hrs, not exceeding about 60 mg to about 120 mg/day).

Administration Regimen
NSAID in Combination with at Least One Lipid Formulated Therapeutic Agent It will be understood that the NSAID and the at least one lipid formulated therapeutic agent are formulated separately and administered sequentially (the NSAID is administered prior to the administration of the at least one lipid formulated therapeutic agent). For purposes of the present disclosure, such administration regimens are considered the administration of an NSAID "in combination with" at least one lipid formulated therapeutic agent.

As described herein, the NSAID is administered prior to at least one lipid formulated therapeutic agent being administered. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 minutes before, or 1 or less than 1 minute before administration of the second component. In certain embodiments, the NSAID is administered within about 3 hours prior to the at least one lipid formulated therapeutic agent being administered. In certain embodiments, the NSAID is administered within about 2 hours prior to the at least one lipid formulated therapeutic agent being administered. In certain embodiments, the NSAID is administered within about 1 hour prior to the at least one lipid formulated therapeutic agent being administered. In certain embodiments, the NSAID is administered within about 30 minutes prior to the at least one lipid formulated therapeutic agent being administered. In certain embodiments, the NSAID is administered within about 20 minutes prior to the at least one lipid formulated therapeutic agent being administered. In certain embodiments, the NSAID is administered within about 10 minutes prior to the at least one lipid formulated therapeutic agent being administered. For example, in certain embodiments, the NSAID is administered intramuscularly or subcutaneously within about 1 hour prior to the at least one lipid formulated therapeutic agent being administered. In certain embodiments, the NSAID is administered intravenously within about 1-2 hours prior to the at least one lipid formulated therapeutic agent being administered.

In certain embodiments, the NSAID is administered at least once prior to the administration of the at least one lipid formulated therapeutic agent. In certain embodiments, the NSAID is administered once prior to the administration of the at least one lipid formulated therapeutic agent.

Administration Regimen of an Additional Therapeutic Agent in Combination with a NSAID or a Lipid Formulated Therapeutic Agent It will be understood that a NSAID and at least one additional therapeutic agent can be formulated together in a single preparation or that they can be formulated separately and, thus, administered separately, either simultaneously or sequentially (the agent(s) may be administered prior to or after the administration of the NSAID). In one embodiment, when the agents are administered sequentially (e.g. at different times), the agents may be administered so that their biological effects overlap (i.e. each agent is producing a biological effect at a single given time). For purposes of the present disclosure, such administration regimens are considered the administration of a NSAID "in combination with" at least one additional therapeutic agent or active component.

It will also be understood that at least one lipid formulated therapeutic agent and at least one additional therapeutic agent can be formulated together in a single preparation or that they can be formulated separately and, thus, administered separately, either simultaneously or sequentially (the agent(s) may be administered prior to or after the administration of the at least one lipid formulated therapeutic agent). In one embodiment, when the agents are administered sequentially (e.g. at different times), the agents may be administered so that their biological effects overlap (i.e. each agent is producing a biological effect at a single given time). For purposes of the present disclosure, such administration regimens are considered the administration of at least one lipid formulated therapeutic agent "in combination with" at least one additional therapeutic agent or active component.

The at least one additional therapeutic agent (additional component) may be administered to a subject prior to administration of a NSAID or at least one lipid formulated therapeutic agent. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the at least one additional therapeutic agent/component may be administered to a subject after administration of a NSAID or at least one lipid formulated therapeutic agent. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In certain embodiments, the additional therapeutic agent is a NSAID, which is administered after the administration of the at least one lipid formulated therapeutic agent (e.g., between about 4 to about 8 hours after the lipid formulated therapeutic agent is administered). In certain embodiments, the additional NSAID may be the same or different from the NSAID administered via injection and may be administered by the same or different route.

In yet other embodiments, the at least one additional therapeutic agent may be administered to a subject concurrent with administration of a NSAID or at least one lipid formulated therapeutic agent. "Concurrent" administration, for purposes of the present invention, includes, e.g., administration of a NSAID or at least one at least one lipid formulated therapeutic agent and the at least one additional therapeutic agent to a subject in a single dosage form (e.g., co-formulated), or in separate dosage forms administered to the subject within about 30 minutes or less of each other. If administered in separate dosage forms, each dosage form may be administered via the same route (e.g., both the NSAID/lipid formulated therapeutic agent and the additional therapeutically active component may be administered intravenously); alternatively, each dosage form may be administered via a different route (e.g., the NSAID may be administered intramuscularly, the lipid formulated therapeutic agent may be administered intravenously, and the additional therapeutically active component may be administered orally). In any event, administering the components in a single dosage from, in separate dosage forms by the same route, or in separate dosage forms by different routes are all considered "concurrent administration" for purposes of the present disclosure. For purposes of the present disclosure, administration of a NSAID/lipid formulated therapeutic agent "prior to", "concurrent with," or "after" (as those terms are defined herein above) administration of an additional therapeutic agent is considered administration of an NSAID/lipid formulated therapeutic agent "in combination with" an additional therapeutic agent).

As described herein, pharmaceutical compositions in which a NSAID or lipid formulated therapeutic agent is co-formulated with at least one additional therapeutic agent using a variety of dosage combinations may also be used.

Kits

One embodiment provides a kit. The kit may comprise a container comprising the combination. Suitable containers include, for example, bottles, vials, syringes, blister pack, etc. The container may be formed from a variety of materials such as glass or plastic. The container may hold the combination which is effective for treating the condition and may have a sterile access port (for example, the container may be an intravenous solution bag or a vial having a stopper pierceable by a hypodermic injection needle).

The kit may further comprise a label or package-insert on or associated with the container. The term "package-insert" is used to refer to instructions customarily included in commercial packages of therapeutic agents that contain information about the indications, usage, dosage, administration, contraindications and/or warnings concerning the use of such therapeutic agents. In one embodiment, the label or package inserts indicates the administration of the NSAID via injection prior to the intravenous administration of the at least one lipid formulated therapeutic agent, for ameliorating an infusion reaction associated with the intravenous administration of the at least one lipid formulated therapeutic agent.

In certain embodiments, the kits are suitable for the delivery of solid oral forms of the therapeutic agents, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit may comprise (a) a first container with one agent contained therein (e.g., a NSAID); and (b) a second container with a second agent contained therein (e.g., a lipid formulated therapeutic agent). Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the therapeutic agents. For example, the kit may further comprise directions for the simultaneous, sequential or separate administration of the therapeutic agents to a patient in need thereof.

In certain other embodiments, the kit may comprise a container for containing separate compositions such as a divided bottle or a divided foil packet, however, the separate compositions may also be contained within a single, undivided container. In certain embodiments, the kit comprises directions for the administration of the separate therapeutic agents. The kit form is particularly advantageous when the separate therapeutic agents are preferably administered in different dosage forms (e.g., oral and parenteral), are administered at different dosage intervals, or when titration of the individual therapeutic agents of the combination is desired by the prescribing physician.

In certain embodiments, the kit comprises a nonsteroidal anti-inflammatory (NSAID) and at least one lipid formulated therapeutic agent, a container, and a package insert or label indicating the administration of the NSAID via injection prior to the intravenous administration of the at least one lipid formulated therapeutic agent, for ameliorating an infusion reaction associated with the intravenous administration of the at least one lipid formulated therapeutic agent. In certain embodiments, the kit comprises at least one additional therapeutic agent.

The invention will now be illustrated by the following non-limiting Examples.

Example 1

Evaluation of LNP in the Conscious Minipig

The objective of this study was to evaluate the effect of intravenous infusion of LNP2 on hemodynamic function in the conscious, freely moving minipig, when administered with or without a bolus intravenous injection of ketorolac or dexamethasone. The LNP formulation used in these studies have the following lipid composition (molar ratios): PEG-lipid (PEG2000-C-DMA (1.1 mol %); Cationic lipid ((6Z, 16Z)-12-((Z)-dec-4-enyl)docosa-6,16-dien-11-yl 5-(dimethyl-amino)pentanoate (54.6 mol %); cholesterol (32.8 mol %); and DSPC (10.9 mol %). A lipid stock was prepared with the appropriate lipids dissolved in 90% ethanol (total concentration 12.24 mg/mL). The siRNA stock was made up in a 20 mM EDTA buffer at 1.215 mg/mL. The two stocks were combined using the Jeffs et al. method, blending in a t-piece and the combined suspension diluted a further 3-fold with Phosphate Buffered Saline, pH 7.4. The sample was then concentrated and buffer exchange performed via tangential flow ultrafiltration (MWCO 100 k, GE Healthcare). The LNP were then sterile filtered (0.2 μm filter). Concentration was determined using RiboGreen Assay and a Varian Cary Eclipse Fluorimeter. Particle size and polydispersity were determined using a Malvern Nano Series Zetasizer.
Methods Four (4) treatment naïve female Gottingen minipigs (Marshall Farms, N.Y.) were surgically implanted with a D70-PCT PhysioTel implantable radiotelemetry transmitter (Data Sciences International, St. Paul, Minn.) to allow for the measurement of physical activity, body temperature, ECG, heart rate, and arterial blood pressure. The pigs were allowed to recover from surgery for at least 7 days prior to use in the study.

Following surgical recovery, the same four pigs (15-20 kg) received a 60-minute intravenous infusion of vehicle (0.9% saline), LNP2, LNP2+ketorolac, or LNP2+dexamethasone as outlined in the Table 1. Each treatment cohort was separated by a 7-day washout period.

TABLE 1

| Cohort | Treatment | siRNA Dose (mg/kg) | Lipid Dose (mg/kg) | Dose Volume (mL/kg) |
|---|---|---|---|---|
| 1 | Vehicle | 0 | 0 | 1 |
| 2 | LNP2 | 0.3 | 3.5 | 1 |
| 3 | LNP2 + ketorolac[†] | 0.3 | 3.5 | 1 |
| 4 | LNP2 + dexamethasone[‡] | 0.3 | 3.5 | 1 |

[†]Ketorolac was administered as an intravenous bolus dose (1 mg/kg), 10 minutes prior to infusion of LNP2.
[‡]Dexamethasone was administered as an intravenous bolus dose (0.3 mg/kg), 10 minutes prior to infusion of LNP2.

Just prior to each infusion and at approximately 1, 3, 6 and 24 hours after the start of each infusion, a mixed venous blood sample was taken, processed to plasma, stored frozen, and used for subsequent analysis of thromboxane B2 (11-dehydrothromboxane B2). Heart rate and arterial blood pressure was continuously recorded from 30 minutes prior to each infusion to 24 hours after the start of each infusion.
Results and Discussion Administration of LNP2 resulted in a profound increase in plasma thromboxane B2 levels at 1 and 3 hours after the start of infusion. The increase in thromboxane B2 was absent in the vehicle control group, was mitigated completely by co-administration with ketorolac, and was reduced, but not completely, by co-administration with dexamethasone (FIG. 1).

Figure 2:
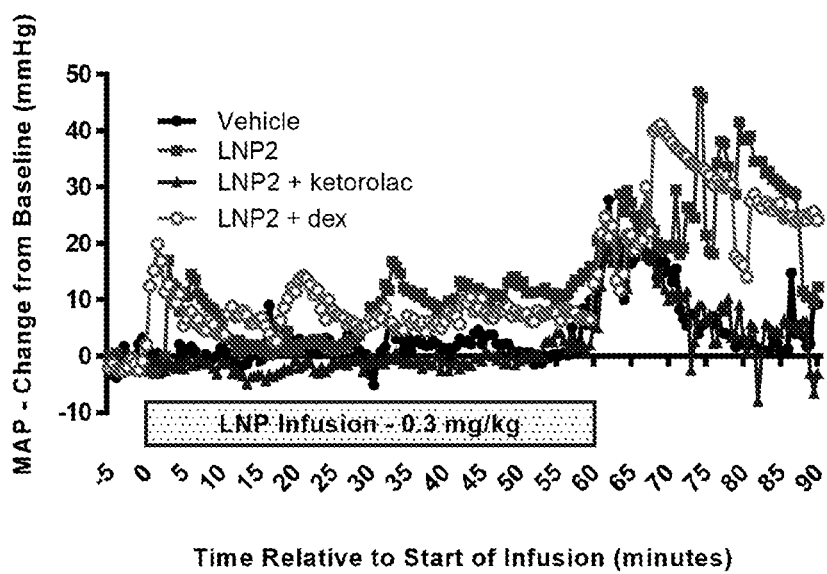
FIG. 2. The effect of LNP2 infusion (with and without ketorolac or dexamethasone) on mean arterial blood pressure in the conscious minipig during the infusion and for the first 30 minutes thereafter. Results are reported in 30 second intervals and are expressed as the mean response (n=4) at each time point.
Figure 3:
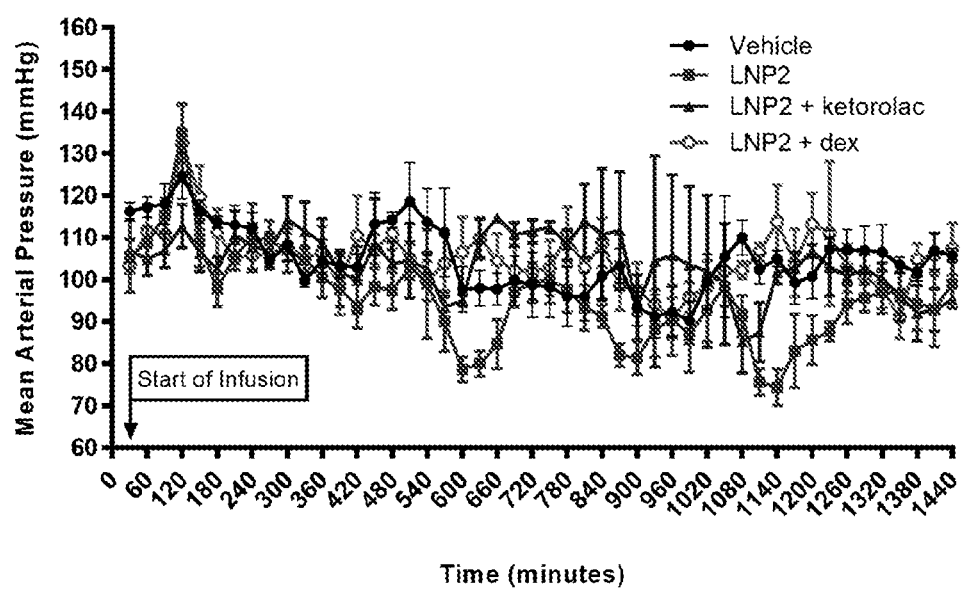
FIG. 3. The effect of LNP2 infusion (with and without ketorolac or dexamethasone) on mean arterial blood pressure in the conscious minipig, recorded for a 24-hour period. Results are reported in 30 minute intervals and are expressed as the mean+/−sem (n=4).

The increase in thromboxane B2 appears to be associated with an overall increase in blood pressure observed with LNP2 during the infusion and shortly thereafter (FIG. 2). The effect of LNP2 on blood pressure was biphasic with an almost immediate increase (~15-20 mmHg) that occurred within minutes of starting the infusion, returning to baseline by 10 minutes, and then gradually increasing, reaching a peak increase of approximately 40 mmHg by 80-85 minutes after the start of infusion. It is noteworthy that this acute infusion reaction to LNP2 was completely prevented by co-administration with ketorolac, but not by dexamethasone. In contrast to the acute hypertensive effects of LNP2 infusion, several episodes of hypotension (lasting 1-2 hours at a time) were observed following LNP2 infusion, starting about 9 hours after the start of infusion (FIG. 3). On each occasion, the average mean arterial pressure was decreased by 20-30 mmHg, relative to vehicle control, and was prevented by co-administration with either ketorolac or dexamethasone.

In conclusion, intravenous infusion of 0.3 mg/kg LNP2 over 60 minutes to conscious female minipigs resulted in an acute infusion reaction that occurred during and shortly after infusion, and was characterized by an elevation of venous thromboxane B2 concentrations, and an increase in blood pressure. A more delayed infusion reaction occurred approximately 8 hours after the end of the infusion, involving several episodes of hypotension. Co-administration of LNP2 with ketorolac completely prevented the acute infusion reaction and effectively mitigated the more delayed hypotension. Co-administration of LNP2 with dexamethasone had minimal to no effect on the acute infusion reaction, but effectively prevented the more delayed hypotension.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of ameliorating an infusion reaction associated with intravenous administration of at least one lipid formulated therapeutic agent in a mammal in need thereof, comprising administering to the mammal via injection a therapeutically effective amount of a nonsteroidal anti-inflammatory (NSAID) prior to the at least one lipid formulated therapeutic agent being intravenously administered, wherein the NSAID is ketorolac, wherein the infusion reaction comprises hypertension followed by hypotension and an increase in plasma thromboxane B2 levels, wherein the at least one lipid formulated therapeutic agent is formulated in a lipid nanoparticle (LNP), and wherein the lipid formulated therapeutic agent is a nucleic acid.

2. The method of claim 1, wherein the administration of the NSAID begins within about 2 hours prior to the administration of the at least one lipid formulated therapeutic agent.

3. The method of claim 1, wherein the ketorolac is administered in a dose of about 15 mg to about 60 mg.

4. The method of claim 3, wherein the ketorolac is administered in a dose of about 30 mg to about 60 mg.

5. The method of claim 1, wherein the at least one lipid formulated therapeutic agent is formulated in a lipid nanoparticle (LNP) comprising:
  a) the at least one therapeutic agent;
  b) a cationic lipid; and
  C) a non-cationic lipid.

6. The method of claim 1, wherein the lipid formulated therapeutic agent is siRNA or mRNA.

7. The method of claim 6, wherein the lipid formulated therapeutic agent is siRNA.

8. The method of claim 6, wherein the lipid formulated therapeutic agent is mRNA.

9. The method of claim 5, further comprising administering an additional therapeutic agent.

10. The method of claim 9, wherein the additional therapeutic agent is dexamethasone.

11. The method of claim 1, wherein the NSAID is administered parenterally, intravenously, intramuscularly or subcutaneously.

* * * * *